(12) United States Patent
Dillavou et al.

(10) Patent No.: US 9,886,552 B2
(45) Date of Patent: Feb. 6, 2018

(54) SYSTEM AND METHOD FOR IMAGE REGISTRATION OF MULTIPLE VIDEO STREAMS

(75) Inventors: Marcus W. Dillavou, Birmingham, AL (US); Phillip Corey Shum, Birmingham, AL (US); Baron L. Guthrie, Birmingham, AL (US); Mahesh B. Shenai, Birmingham, AL (US); Drew Steven Deaton, Birmingham, AL (US); Matthew Benton May, Birmingham, AL (US)

(73) Assignee: HELP LIGHTING, INC., Birmingham, AL (US)

( * ) Notice: Subject to any disclaimer, the term of this patent is extended or adjusted under 35 U.S.C. 154(b) by 0 days.

(21) Appl. No.: 13/208,926

(22) Filed: Aug. 12, 2011

(65) Prior Publication Data
US 2013/0038632 A1 Feb. 14, 2013

(51) Int. Cl.
| | |
|---|---|
| G09G 5/00 | (2006.01) |
| G06F 19/00 | (2011.01) |
| G06F 3/14 | (2006.01) |
| H04N 13/00 | (2006.01) |
| G09G 3/00 | (2006.01) |
| G09G 5/397 | (2006.01) |

(52) U.S. Cl.
CPC ........ *G06F 19/3437* (2013.01); *G06F 3/1431* (2013.01); *G06F 19/3418* (2013.01); *G06F 19/3425* (2013.01); *G06F 19/3481* (2013.01); *H04N 13/0048* (2013.01); *H04N 13/0051* (2013.01); *H04N 13/0059* (2013.01); *G09G 3/003* (2013.01); *G09G 5/397* (2013.01); *G09G 2340/02* (2013.01); *G09G 2370/045* (2013.01); *G09G 2380/08* (2013.01)

(58) Field of Classification Search
CPC ....... G06T 19/006; G06T 19/00; G06F 3/011; G06F 3/012; G02B 27/017
USPC ........... 345/8, 157, 419, 427, 428, 475, 633; 382/103, 154; 348/208, 169, 46; 703/6
See application file for complete search history.

(56) References Cited

U.S. PATENT DOCUMENTS

| | | | |
|---|---|---|---|
| 3,931,679 A | 1/1976 | Carter | 32/71 |
| 4,601,664 A | 7/1986 | Bertino | 434/264 |

(Continued)

FOREIGN PATENT DOCUMENTS

| | | |
|---|---|---|
| AU | 2008270883 | 5/2008 |
| AU | 2012295324 A1 | 3/2014 |

(Continued)

OTHER PUBLICATIONS

U.S. Appl. No. 60/735,458, filed Nov. 11, 2005, Danny Murphy.

(Continued)

*Primary Examiner* — Abderrahim Merouan
(74) *Attorney, Agent, or Firm* — Michael J. Riesen; Baker Hostetler LLP

(57) ABSTRACT

Provided herein are methods and systems for image registration from multiple sources. A method for image registration includes rendering a common field of interest that reflects a presence of a plurality of elements, wherein at least one of the elements is a remote element located remotely from another of the elements and updating the common field of interest such that the presence of the at least one of the elements is registered relative to another of the elements.

18 Claims, 20 Drawing Sheets

(56) References Cited

U.S. PATENT DOCUMENTS

| | | | |
|---|---|---|---|
| 4,970,666 A | 11/1990 | Welsh | 364/522 |
| 5,102,340 A | 4/1992 | Berlinghoff | 434/263 |
| 5,391,081 A | 2/1995 | Lampotang | 434/262 |
| 5,403,192 A | 4/1995 | Kleinwaks | 434/272 |
| 5,584,701 A | 12/1996 | Lampotang | 434/272 |
| 5,668,608 A | 9/1997 | Lee | |
| 5,769,641 A | 6/1998 | Lampotang | 434/272 |
| 5,772,442 A | 6/1998 | Lampotang | 434/265 |
| 5,779,484 A | 7/1998 | Lampotang | 434/266 |
| 5,853,292 A | 12/1998 | Eggert | 434/262 |
| 5,868,579 A | 2/1999 | Lampotang | 434/266 |
| 5,882,207 A | 3/1999 | Lampotang | 434/268 |
| 5,890,908 A | 4/1999 | Lampotang | 434/268 |
| 5,900,923 A | 5/1999 | Prendergast | 351/221 |
| 5,941,710 A | 8/1999 | Lampotang | 434/272 |
| 6,042,477 A | 3/2000 | Addink | |
| 6,157,677 A | 12/2000 | Martens et al. | |
| 6,166,744 A | 12/2000 | Jaszlics | 345/435 |
| 6,193,519 B1 | 2/2001 | Eggert | 434/262 |
| 6,220,866 B1 | 4/2001 | Amend | 434/266 |
| 6,241,609 B1 | 6/2001 | Rutgers | 463/31 |
| 6,246,975 B1 | 6/2001 | Rivonelli | 705/11 |
| 6,257,234 B1 | 7/2001 | Sun | 128/204.18 |
| 6,273,728 B1 | 8/2001 | Van Meurs | 434/262 |
| 6,293,519 B1 | 9/2001 | Farretta | |
| 6,301,339 B1 | 10/2001 | Staples | 379/93.01 |
| 6,317,165 B1 | 11/2001 | Balram et al. | |
| 6,443,735 B1 | 9/2002 | Eggert | 434/262 |
| 6,461,165 B1 | 10/2002 | Takushma | 434/265 |
| 6,503,087 B1 | 1/2003 | Eggert | 434/262 |
| 6,527,558 B1 | 3/2003 | Eggert | 434/327 |
| 6,535,714 B2 | 3/2003 | Melker | 434/350 |
| 6,570,563 B1 | 5/2003 | Honda | |
| 6,608,628 B1* | 8/2003 | Ross et al. | 345/619 |
| 6,692,258 B1 | 2/2004 | Kurzweil | 434/262 |
| 6,697,451 B2 | 2/2004 | Acharya | 378/18 |
| 6,747,672 B1 | 6/2004 | Haakonsen | 345/700 |
| 6,747,674 B1 | 6/2004 | Asami | |
| 6,758,676 B2 | 7/2004 | Eggert | 434/262 |
| 6,774,855 B2 | 8/2004 | Bateman et al. | |
| 6,774,885 B1 | 8/2004 | Even-Zohar | 345/156 |
| 6,780,016 B1 | 8/2004 | Toly | 434/262 |
| 6,921,267 B2 | 7/2005 | Van Oostrom | 434/272 |
| 7,015,954 B1 | 3/2006 | Foote | 348/218.1 |
| 7,181,690 B1 | 2/2007 | Leahy et al. | |
| 7,190,331 B2* | 3/2007 | Genc et al. | 345/9 |
| 7,259,761 B2 | 8/2007 | Shih | 345/419 |
| 7,367,809 B2* | 5/2008 | Takahashi | G06F 19/3437 348/E13.014 |
| 7,373,377 B2 | 5/2008 | Altieri | 709/203 |
| 7,376,903 B2 | 5/2008 | Morita | 715/757 |
| 7,403,664 B2 | 7/2008 | Porikli et al. | |
| 7,728,852 B2* | 6/2010 | Suzuki et al. | 345/632 |
| 7,728,868 B2 | 6/2010 | Razzaque | 348/77 |
| 7,787,927 B2 | 8/2010 | Wood | 600/410 |
| 7,815,644 B2* | 10/2010 | Masini | 606/86 R |
| 7,949,616 B2 | 5/2011 | Levy | 705/34 |
| 8,046,408 B2 | 10/2011 | Torabi | 709/203 |
| 8,179,412 B2 | 5/2012 | Swanson | |
| 8,336,777 B1 | 12/2012 | Pantuso et al. | |
| 8,385,687 B1* | 2/2013 | Blais-Morin | 382/294 |
| 8,398,541 B2* | 3/2013 | Dimaio et al. | 600/111 |
| 8,520,024 B2 | 8/2013 | Guthrie et al. | |
| 8,902,248 B1 | 12/2014 | Bidarkar et al. | |
| 9,020,203 B2 | 4/2015 | Dillavou et al. | |
| 2001/0026630 A1 | 10/2001 | Honda | |
| 2002/0049510 A1* | 4/2002 | Oda | B25J 9/1689 700/114 |
| 2003/0219146 A1 | 11/2003 | Jepson et al. | |
| 2004/0009459 A1 | 1/2004 | Anderson | 703/11 |
| 2004/0091845 A1 | 5/2004 | Azerad | 434/263 |
| 2004/0161731 A1 | 8/2004 | Arington et al. | |
| 2004/0189701 A1 | 9/2004 | Badt | 345/753 |
| 2004/0193441 A1 | 9/2004 | Altieri | 709/203 |
| 2004/0260170 A1 | 12/2004 | Wood | 600/410 |
| 2005/0074154 A1 | 4/2005 | Georgescu et al. | |
| 2005/0197818 A1 | 9/2005 | Monfared | 703/21 |
| 2005/0203367 A1* | 9/2005 | Ahmed et al. | 600/407 |
| 2005/0203380 A1 | 9/2005 | Sauer et al. | |
| 2005/0267778 A1 | 12/2005 | Kazman | 705/1 |
| 2005/0273185 A1 | 12/2005 | Teiwes et al. | |
| 2005/0289472 A1 | 12/2005 | Morita | 715/757 |
| 2006/0187224 A1 | 8/2006 | Ehrlich | |
| 2007/0018975 A1* | 1/2007 | Chuanggui et al. | 345/419 |
| 2007/0048702 A1 | 3/2007 | Jang | 434/224 |
| 2007/0055578 A1 | 3/2007 | Ashton | 705/26 |
| 2007/0064098 A1 | 3/2007 | Tran | 345/6 |
| 2007/0149290 A1 | 6/2007 | Nickell | 463/42 |
| 2007/0248261 A1 | 10/2007 | Zhou et al. | |
| 2008/0024594 A1* | 1/2008 | Ritchey | 348/36 |
| 2008/0025640 A1 | 1/2008 | Trudeau et al. | |
| 2008/0055305 A1* | 3/2008 | Blank et al. | 345/419 |
| 2008/0079752 A1 | 4/2008 | Gates et al. | |
| 2008/0123910 A1* | 5/2008 | Zhu | 382/128 |
| 2008/0123927 A1* | 5/2008 | Miga et al. | 382/131 |
| 2008/0158333 A1 | 7/2008 | Krisbergh et al. | |
| 2008/0231626 A1 | 9/2008 | Mohamed et al. | |
| 2008/0278633 A1 | 11/2008 | Tsoupko-Sitnikov et al. | |
| 2009/0058987 A1 | 3/2009 | Thielman et al. | |
| 2009/0287089 A1 | 11/2009 | Spector | 600/443 |
| 2009/0300122 A1 | 12/2009 | Freer | |
| 2010/0141555 A1 | 6/2010 | Rorberg et al. | |
| 2010/0226564 A1* | 9/2010 | Marchesotti | G06F 17/30256 382/159 |
| 2010/0241953 A1* | 9/2010 | Kim | H04N 21/85406 715/256 |
| 2010/0295921 A1* | 11/2010 | Guthrie et al. | 348/14.08 |
| 2010/0315418 A1 | 12/2010 | Woo | |
| 2011/0018959 A1 | 1/2011 | Friel et al. | |
| 2011/0084983 A1 | 4/2011 | Demaine | |
| 2011/0116703 A1* | 5/2011 | Fu et al. | 382/132 |
| 2011/0135206 A1* | 6/2011 | Miura | G06T 5/50 382/201 |
| 2011/0183182 A1 | 7/2011 | Woehrle et al. | |
| 2011/0188744 A1 | 8/2011 | Sun | |
| 2011/0216060 A1 | 9/2011 | Weising et al. | |
| 2011/0249029 A1* | 10/2011 | Baumgart | G06T 3/0068 345/648 |
| 2011/0270135 A1* | 11/2011 | Dooley et al. | 600/595 |
| 2012/0133786 A1* | 5/2012 | Watanabe | G06T 7/0024 348/208.4 |
| 2012/0201456 A1 | 8/2012 | El-Mahdy et al. | |
| 2012/0263154 A1 | 10/2012 | Blanchflower et al. | |
| 2012/0320157 A1 | 12/2012 | Junuzovic et al. | |
| 2012/0324332 A1* | 12/2012 | Zaragoza | G06F 9/4443 715/234 |
| 2013/0038632 A1 | 2/2013 | Dillavou et al. | |
| 2013/0083063 A1 | 4/2013 | McCulloch | |
| 2013/0308827 A1 | 11/2013 | Dillavou et al. | |
| 2014/0176533 A1 | 6/2014 | Dillavou et al. | |
| 2015/0002541 A1 | 1/2015 | Dillavou et al. | |

FOREIGN PATENT DOCUMENTS

| | | |
|---|---|---|
| CA | 2694095 | 5/2008 |
| CN | 200880024323.7 | 5/2008 |
| CN | 101405769 A1 | 4/2009 |
| CN | 101743567 | 6/2010 |
| CN | 104011741 A | 8/2014 |
| EP | 1804209 | 7/2007 |
| EP | 8826034 | 5/2008 |
| EP | 8826034.4 | 5/2008 |
| EP | 2163092 | 3/2010 |
| EP | 2742461 A1 | 6/2014 |
| HK | 10111098.6 | 11/2010 |
| HK | 1144608 | 2/2011 |
| IN | 7420/CHENP/2009 | 5/2008 |
| JP | 05227463 A | 9/1993 |
| JP | 2002074370 A | 3/2002 |
| JP | 2007535875 A | 12/2007 |
| JP | 2010-508631 | 5/2008 |
| JP | 2009134693 A | 6/2009 |
| JP | 2010141476 A | 6/2010 |

(56) References Cited

FOREIGN PATENT DOCUMENTS

| | | |
|---|---|---|
| JP | 2010-528354 | 8/2010 |
| JP | 2013-024298 A | 2/2013 |
| NZ | 582133 | 5/2008 |
| NZ | 621149 A | 12/2015 |
| WO | WO 1996/009722 | 3/1996 |
| WO | 00/48475 A1 | 8/2000 |
| WO | WO 2000/049475 | 8/2000 |
| WO | WO 2005/119554 | 12/2005 |
| WO | WO 2006/108279 | 10/2006 |
| WO | PCT/US2006/060853 | 11/2006 |
| WO | WO 2007/059477 | 5/2007 |
| WO | PCT/US2008/064118 | 5/2008 |
| WO | WO 2009/005901 | 1/2009 |
| WO | PCT/US2012/050238 | 8/2012 |
| WO | 2013/025457 A1 | 2/2013 |
| WO | 2013/177125 A2 | 11/2013 |
| WO | 2014/105961 A1 | 7/2014 |

OTHER PUBLICATIONS

U.S. Appl. No. 60/764,508, filed Feb. 2, 2006, Danny Murphy.
U.S. Appl. No. 60/930,874, filed May 18, 2007, Barton Guthrie.
U.S. Appl. No. 12/600,805, filed May 19, 2008, Barton Guthrie.
U.S. Appl. No. 13/476,712, filed May 21, 2012, Vipaar, LLC (Marcus W. Dillavou).
U.S. Appl. No. 13/727,202, filed Dec. 26, 2012, Marcus W. Dillavou.
U.S. Appl. No. 13/476,712, filed May 21, 2012, Dillavou.
U.S. Appl. No. 13/727,202, filed Dec. 26, 2012, Dillavou.
Ai, et al. "Tele-immersive medical educational environment," University of Illinois at Chicago. VRMedLab, School of Biomedical and Health Information Sciences: p. 1-7.
Ballantyne, et al. "The da Vinci telerobotic surgical systems: the virtual operative field and telepresence surgery" Surg Clin North Am. 2003, 83 (6): p. 1293-1304.
Billinghurst, et al. "Mixing realities in shared space: an augmented reality interface for collaborative computing," Multimedia and Expo 2000, 3: p. 1641-1644.
Billinghurst, et al. "Real world teleconferencing," IEEE Computer Graphics 2002, 22(6): p. 11-13.
Birkfellner, et al. "Computer-enhanced stereoscopic vision in a head-mounted operating binocular," Phys Med Biol 2003, 48 (3): p. N49-57.
Dangelmaier, et al. "Virtual and augmented reality support for discrete manufacturing system simulation," Computers in Industry 2005, 56 (4): p. 371-383.
Gibson, et al. "Simulating arthroscopic knee surgery using volumetric object representations, real-time vol. rendering and haptic feedback," Proceedings of CVRMed-MRCAS 1997: p. 369-378.
Haluck, et al. Reliability and validity of endotower, a virtual reality trainer for angled endoscope navigation. *J.D. Westwood et al. (Eds)*, Meidcine Meets Virtual Reality 2002, IOS Press: p. 1-6.
Kurosaki, et al. "Skill transmission for hand positioning task through view-sharing system," Graduate School of Information Science and Technology, Osaka University: p. 1-4.
Nicolau, et al. "An augmented reality system to guide radio-frequency tumour ablation," Computer Animation and Virtual World (previously the Journal of Visualization & Computer Animation) 2004, 16 (1): p. 1-10, 200.
Nishikawa, et al. Mutual view sharing system for real-time tele-communication, Systems and Computers in Japan 2006, 37 (14): p. 292-304.
Paul, et al. "Augmented virtuality based on stereoscopic reconstruction in multimodal image-guided neurosurgery: methods and performance evaluation," IEEE Trans Med Imaging 2005, 24 (11): p. 1500-1511.
Satava, R.M. "Medical applications of virtual reality," J Med Systems 1996, 19: p. 275-280.
Shuhaiber, J.H. "Augmented reality in surgery," Arch Surg. 2004, 139 (2): p. 170-174.
Soler, et al. "Virtual reality, augmented reality and robotics in surgical procedures of the liver," Th. M. Buzug and T.C. Lueth, editors. Perspectives in Image-guided Surgery 2004: p. 476-484.
Stafford, et al. "User evaluation of God-like interaction techniques," Proc. 9th Australasian User Interface Conference (AUIC2008), School of Computer and Information Science, University of South Australia: p. 19-28.
Taffinder, et al. "Validation of virtual reality to teach and assess pscyhomotor skills in laparascopic surgery: results from randomized controlled studies using the MIST VR laparoscopic simulator," Medicine Meets Virtual Reality 1998: p. 124-133.
Theoktisto, et al. "Enhancing collaboration in virtual reality applications," Computers and Graphics 2005, 29 (5): p. 704-718.
Viciana-Abad, et al. "A preliminary study of presence in virtual reality training simulation for medical emergencies," Medicinal Meets Virtual Reality 2004, 12: p. 394-396.
Vogt, et al. "An ar system with intuitive user interface for manipulation and visualization of 3d medical data," Stud Health Technol Inform. 2004, 98: p. 397-403.
Wann, et al. "Natural problems for stereoscopic depth perception in virtual environments," Vision Research 1995, 35 (19): p. 2731-2736.
International Preliminary Report on Patenability issued on May 14, 2008 by the International Searching Authority for Application No. PCT/US2006/060853, filed Nov. 13, 2006 (Applicant—UAB Research Foundations; Inventor—Danny Murphy;) (p. 1-6).
International Search Report and Written Opinion issued on Feb. 6, 2008 by the International Searching Authority for Application No. PCT/US2006/060853, filed Nov. 13, 2006 (Applicant—UAB Research Foundations; Inventor—Danny Murphy;) (p. 1-9).
Examiner's First Report issued Mar. 29, 2012 by IP Australia for Application No. 2008270883, filed May 19, 2008 (Applicant—UAB Research Foundation; Inventor—Guthrie, et al.;) (p. 1-2).
Request for Examination and Request to Postpone filed Mar. 3, 2011 to IP Australia for Application No. 2008270883 filed May 19, 2008 (Applicant—UAB Research Foundation; Inventor—Guthrie, et al.;) (p. 1-18).
Request for Examination of Patent issued Sep. 14, 2010 by IP Australia for Application No. 2008270883, filed May 19, 2008 (Applicant—UAB Research Foundation; Inventor—Guthrie, et al.;) (p. 1-1).
Response to Postponing Request issued Mar. 7, 2011 by IP Australia for Application No. 2008270883, filed May 19, 2008 (Applicant—UAB Research Foundation; Inventor—Guthrie, et al.;) (p. 1-1).
First Office Action issued Jun. 23, 2011 by the State Intellectual Property Office of the People's Republic of China for Application No. 2008800243237, filed May 19, 2080 (Applicant—UAB Research Foundation; Inventor—Guthrie, et al.;) (pp. 1-68).
Notification of Passing Preliminary Examination issued Apr. 17, 2010 by the State Intellectual Property Office of the People's Republic of China for Application No. 2008800243237 filed May 19, 2008 (Applicant—UAB Research Foundation; Inventor—Guthrie, et al.;) (pp. 1-2).
Response to First Office Action filed Nov. 1, 2011 for Application No. 2008800243237, filed May 19, 2008 (Applicant—UAB Research Foundation; Inventor—Guthrie, et al.; ) (p. 1-5).
Response to Second Office Action filed Aug. 15, 2012 for Application No. 2008800243237, filed May 19, 2008 (Applicant—UAB Research Foundation; Inventor—Guthrie, et al.;) (p. 1-5).
Second Office Action issued May 3, 2012 by the State Intellectual Property Office of the People's Republic of China for Application No. 2008800243237, filed May 19, 2008 (Applicant—UAB Research Foundation; Inventor—Guthrie, et al.;) (p. 1-8).
Third Office Action issued Dec. 28, 2012 by the State Intellectual Property Office of the People's Republic of China for Application No. 2008800243237, filed May 19, 2008 (Applicant—UAB Research Foundation; Inventor—Guthrie, et al.;) (p. 1-5).
Amendments filed Apr. 4, 2012 to the European Patent Office for Application No. 20080826034, filed May 19, 2008 (Applicant—UAB Research Foundation; Inventor—Guthrie, et al.;) (p. 1-14).

(56) References Cited

OTHER PUBLICATIONS

Communication from the Examining Division issued Jun. 8, 2012 by the European Patent Office for Application No. 20080826034, filed May 19, 2008 (Applicant—UAB Reserach Foundation; Inventor—Guthrie, et al.;) (p. 1-8).
Communication Regarding Possible Amendments of Claims issued Jan. 13, 2010 by the European Patent Office for Application No. 20080826034, filed May 19, 2008 (Applicant—UAB Research Foundation; Inventor—Guthrie, et al.;) (p. 1-2).
European Search Report issued on Sep. 15, 2011 by the European Patent Office for Application No. 2008826034, filed May 19, 2008 (Applicant—UAB Research Foundations; Inventor—Barton Guthrie;) (p. 1-8).
Invitation Pursuant to Rule 62a(1) issued May 16, 2011 by the European Patent Office for Application No. 20080826034, filed May 19, 2008 (Applicant—UAB Research Foundation; Inventor—Guthrie, et al.;) (p. 12).
Office Action issued Feb. 10, 2012 by Japan Patent Office for Application No. 2010/508631, filed May 19, 2008 (Applicant—UAB Research Foundation; Inventor—Guthrie, et al.;) (p. 1-4).
Response and Amendment filed Feb. 23, 2010 to the European Patent Office for Application No. 20080826034, filed May 19, 2008 (Applicant—UAB Research Foundation; Inventor—Guthrie, et al.;) (p. 1-10).
Response and Amendment filed Oct. 17, 2012 by the European Patent Office for Application No. 08826034.4, filed May 19, 2008 (Applicant—UAB Research Foundation; Inventor—Guthrie, et al.;) (p. 1-16).
Final Office Action issued Oct. 12, 2012 for Application No. 2010-508631, filed May 19, 2008 (Applicant—UAB Research Foundation; Inventor—Guthrie, et al.;) (p. 1-2).
Official Action issued Feb. 10, 2012 by the Japanese Patent Office for Application No. 2010-508631, filed May 19, 2008 (Applicant—UAB Research Foundation; Inventor—Guthrie, et al.;) (p. 1-4).
Response to Official Action filed Aug. 10, 2012 for Application No. 2010508631, filed May 19, 2008 (Applicant—UAB Research Foundation; Inventor—Guthrie, et al.;) (p. 1-5).
Voluntary Amendment filed Jan. 15, 2010 to Japan Patent Office for Application No. 2010/508631, filed May 19, 2008 (Applicant—UAB Research Foundation; Inventor—Guthrie, et al.;) (p. 1-14).
Examination Report issued May 3, 2011 by the New Zealand Intellectual Property Office for Application No. 582133, filed May 19, 2008 (Applicant—UAB Research Foundation; Inventor—Guthrie, et al.;) (p. 1-2).
Examination Report and Notice of Acceptance issued Dec. 3, 2012 by the New Zealand Intellectual Property Office for Application No. 582133, filed May 19, 2008 (Applicant—UAB Research Foundation; Inventor—Guthrie, et al.;) (p. 1-1).
Response to Examination Report filed Nov. 19, 2012 for Application No. 582133, filed May 19, 2008 (Applicant—UAB Research Foundation; Inventor—Guthrie, et al.;) (p. 1-8).
International Preliminary Report on Patenability issued on Nov. 24, 2009 by the International Searching Authority for Application No. PCT/US2008/064118, filed May 19, 2008 (Applicant—UAB Research Foundations; Inventor —Barton Guthrie;) (p. 1-6).
International Search Report and Written Opinion issued on Dec. 17, 2008 by the International Searching Authority for Application No. PCT/US2008/064118, filed May 19, 2008 (Applicant—UAB Research Foundations; Inventor—Barton Guthrie;) (p. 1-8).
Non-Final Office Action issued Nov. 23, 2012 by the United States Patent and Trademark Office for Application No. 12/600,805, filed Aug. 11, 2010 (Applicant—UAB Research Foundation; Inventor—Guthrie, et al.;) (p. 1-25).
International Search Report and Written Opinion issued on Oct. 16, 2012 by the International Searching Authority for Application No. PCT/US12/50238, filed Aug. 10, 2012 (Applicant—Vipaar, LLC; Inventor—Marcus W. Dillavou;) (p. 1-12).
Newman et al. A Desk Supporting Computer-based Interaction with Paper Documents; Rank Xerox EuroPARC, United Kingdom, 1992 ACM 0-89791-513-5/92/0005-0587, pp. 587-592.
Greenberg, An Annotated Bibliography of Computer Supported Cooperative Work, SIGCHI Bulletin, Jul. 1991, vol. 23, No. 3, pp. 29-62.
Ishii et al. ClearBoard: A Seamless Medium for Shared Drawing and Conversation with Eye Contact, NTT Human Interface Laboraties, Kanagawa, Japan, 1992 ACM 0-89791-513-5/92/0005-0525, pp. 525-532, Exh. 705-706.
Takemura et al. Cooperative Work Environment Using Virtual Workspace, ATR Communication Systems Research Laboratories, Kyoto, Japan, 1992 ACM 0-89791-543-7/92/0226; CSCW 92 Proceedings, Nov. 1992, pp. 226-232.
Greenberg, CSCW '92 Formal Video Program, Department of Computer Science, University of Calgary, 1992, pp. 9-10.
Chang, et al., Design and Model for a Computer Supported Cooperative Environment for CASE and CAD Applications, Department of Computer Science and Engineering, Auburn University, 1997 ACM 0-8971-925-4, pp. 191-198.
Streitz et al., DOLPHIN: Integrated Meeting Support Across Local and Remote Desktop Environments and LiveBoards, IPSI—Integrated Publication and Information Systems Institute, GMD—German National Research Center for Computer Science, Conference Paper Oct. 1994, 1994 ACM 0-89791-xxx-x/xx/xxxx; pp. 1-14.
Ishii, et al., Beyond Videophones: Team WorkStation-2 for Narrowband ISDN, NTT Human Interface Laboratories, Japan; Proceedings of the Third European Conference on Computer supported Cooperative Work Sep. 13-17, 1993, Milan, Italy, ESCSW '93, pp. 325-326.
Ishii, et al., Integration of Interpersonal Space and Shared Workspace: ClearBoard Design and Experiments, NTT Human Interface Laboraties and University of California, Irvine, ACM Transactions on Information Systems, vol. 11, No. 4, Oct. 1993, pp. 349-375.
Yamazaki, et al., GestureLaser and GestureLaser Car, Devleopment of an Embodied Space to Support Remote Instruction, Proceedings of the Sixth European Conference on Computer-Supported Cooperative Work, Sep. 12-16, 1999, Copehangen Denmark; 1999 Kluwer Academic Publishers, pp. 239-258.
Hayne, et al., Implementing Gesturing With Cursors in Group Support Systems, Journal of Management Information Systems, Winter 1993-94, vol. 10, No. 3, pp. 43-61.
Ishii et al., Iterative Design of Seamless Collaboration Media, Communications of the ACM, Aug. 1994, vol. 17, No. 8, pp. 83-97.
Ishii et al., Towawrd An Open Shared Workspace: Computer and Video Fusion Approach of Teamworkstation, Communications of the ACM, Dec. 1991, vol. 34, No. 12, pp. 37-50.
Ishii, Integration of Shared Workspace and Interpersonal Space for Remote Collaboration, Computer Supported Cooperative Work, 1999 John Wiley & Sons, Ltd. pp. 83-101.
Ishii, Translucent Multiuser Interface for Realtime Collaboration, IEICE trans. Fundamentals, vol. E75-A, No. 2 Feb. 1992, pp. 122-131.
DeVincezi, et al., Kinected Conference: Augmenting Video Imaging with Calibrated Depth and Audio, CSCW 2011, Mar. 19-23, 2011, Hangzhou, China, ACM 978-1-4503-0556-3/11/03, pp. 621-624.
Foreman, Managing Data in Distributed Multimedia Conferencing Applications, IEEE MultiMedia, Oct.-Dec. 2002, pp. 30-37.
Kuzuoka, Spatial Workspace Collaboration: A Sharedview Video Support System For Remote Collaboration Capability, Department of Mechano-Informatics, University of Tokyo, 1992 ACM 0-89791-513-5/92/005-0533, pp. 533-540.
Apperley, et al. Use of Video Shadow for Small Group Interaction Awareness on a Large Interactive Display Surface, The Computer Science Department, University of Waikato, New Zealand, 2002, Australian Computer Society, Inc., 10 pgs.
Kling, Cooperation, Coordination and Control in Computer-Supported Work, Communications of the ACM, Dec. 1991, vol. 34, No. 12, pp. 83-88.
Rosenberg, Update on National Science Foundation Funding Of The "Collaboratory", Communications of the ACM, Dec. 1991, vol. 34, No. 12, p. 83.
Norman, Collaborative Computing: Collaboration First, Computing Second, Communications of the ACM, Dec. 1991, vol. 34, No. 12, pp. 88-90.

(56) References Cited

OTHER PUBLICATIONS

Press, Collective Dynabases, Communications of the ACM, Jun. 1992, vol. 35, No. 6, pp. 26-32.
Reeves et al., Supporting Communication Between Designers with Artifact-Centered Evolving Information Spaces, Department of Computer Science and Institute of Cognitive Science, University of Color-401ado, 1992 ACM 0-89791-543-7/92/0010/0394, CSCW 92 Proceedings, Nov. 1992, p. 394.
Tani et al., Courtyard: Integrating Shared Overview on a Large Screen and Per-User Detail on Individual Screens, Hitachi Research Laboratory, Hitachi, Ltd., Human Factors in Computing Systems, 1994 ACM 0-89791-650-6/94/0044, pp. 44-50.
Takemura et al., Cooperative Work Environment Using Virtual Workspace, ATR Communication Systems Research Laboratories, 1992 ACM 0-089791-543-7/92/0010/0226, CSCW 92 Proceedings, Nov. 1992, pp. 226-232.
Wellner, Interacting With Paper on The Digital Desk, Communication of the ACM, Jul. 1993, vol. 36, No. 7, pp. 87-96.
Wiberg, RoamWare: An Integrated Architecture for Seamless Interaction In Between Mobile Meetings, Department of Informatics, Umea University, Sweden, 2001 acm 1-58113-294-08/01/0009, pp. 288-297.
Veltman, Frontiers in Electronic Media, Interactions Jul. & Aug. 1997, pp. 32-66.
Fouss, et al., Classifying Groupware, Department of Computer Science and Software Engineering, Auburn University, 2000 ACM 1-58113-250-6/00/0004, pp. 117-124.
Mandviwalla et al., What Do Groups Need? A Proposed Set of Generic Groupware Requirements, 1994 ACM 1073-0516/94/0900-0245, ACM Transactions on Computer-Human Interaction, vol. 1, No. 3, Sep. 1994, pp. 245-268.
Bly, et al., Media Spaces: Bringing People Together in a Video, Audio, and Computing Environment, Communications of the ACM, Jan. 1993, vol. 36, No. 1, pp. 27-47.
Ishii, et al., Integration of Inter-personal Space and Shared Workspace: ClearBoard Design and Experiments, NTT Human Interface Laboratories and University of California, Irvine, CSCW 92 Proceedings, Nov. 1992, pp. 33-42.
Allen, Groupware and social Reality, Department of Information and Computer Science, University of California, Irvine, Computers & Society, vol. 22, No. 1-4, Oct. 1992, pp. 24-28.
Hunter, et al., WaaZam! Supporting Creative Play at a Distance in Custo-1206mized Video Environments, CHI 2014, Apr. 26-May 1, 2014, Toronto, ACM 978-1-4503-2473-1/14/04, pp. 1197-1206.
Franck, et al., Putting Innovation to Work: Adoption Strategies for MultiMedia Communication Systems, Communication of the ACM, Dec. 1991, vol. 34, No. 12, pp. 53-63.
Gross, Recognizing and Interpreting Diagrams in Design, Division of Environmental Design and Institute of Cognitive Science, University of Colorado, 1994 ACM 0-89791-733-2/94/0010, pp. 88-94.
Chong et al., "A Collaborative multi-site Teleoperation over an ISDN", Mechatronics, Pergamon Press, Oxford, GB, vol. 13, No. 8-9, pp. 957-979, 2002.

Yonekura et al., "Peer-to-Peer Networked Field Type Virtual Environment by Using AtoZ" Cyberworlds,2004 International Conference on Tokyo, Japan Nov. 18-20, 2004, pp. 241-248.
Yonekura T et al., "Peer to Peer Networked Field-type virtual Environment by Using AtoZ", Cyberworlds, 2004 International Conference on Tokyo, Japan, Nov. 18-20, 2004, Piscataway, NJ, USA, IEEE, Nov. 18, 2004, pp. 241-248.
So, Experimental Studies Of the Use of Phase Lead Filters to Compensate Lags in Head—Coupled Visual Displays, IEEE Transactions on Systems, Man, and Cybernetics—Part A: Systems and Humans, 1996, vol. 26, No. 4, pp. 445-454.
Shenai Mahesh B et al., "Virtual Interactive Presence and Augmented Reality (VIPAR) for Remote Surgical Assistance", Neurosurgery, Williams & Wilkins, Baltimore, MD, USA, vol. 68, No. 3, Suppl. 3, Mar. 1, 2011, pp. 200-2007.
Pendergast, A Comparative Analysis of Groupware Application Protocols, ACM SIGCOMM, Computer Communication Review, pp. 28-40.
Kobayashi et al., DispLayers: Multi-Layer display Technique to Enhance Selective Looking of Overlaid Images, NTT Human Interface Laboraties, Kanagawa, Japan, p. 66.
James Davis et al., "The Effects of Time Lag on Driving Performance and a Possible Mitigation", IEEE Transactions On Robotics, IEEE Service Center, Piscataway, NJ, USA, vol. 26, No. 3, Jun. 1, 2010, pp. 590-593.
Ishii, Position Paper for ECSCW '91 Workshop on Open CSCW Systems Toward An Open Shared Workspace: Computer and Video Fusion Approach of Team Workstation, NTT Human Interface Laboratories, Kanagawa, Japan, 4 pgs.
Hamza-Lup, F.G., "A distrubuted augmented reality system for medical training and simulation," Article Retrieved from the Internet. <URL: http://web.archive.org/web/20070416201920/http://www.cs.ucf.edu/-ceh/Publ-ications/Papers/Content/Link04Hamza-LupRollandHughes.pdf> pp. 1-8, (2008).
Graves, et al. Supporting Learners In A Remote CSCL Environment: the Importance of Task and Communication, Dept. Of Computer Science, University of British Columbia, 11 pgs.
Chong N Y et al., "A Collaborative Multi-site Teleoperation Over an ISDN", Mechatronics, Pergamon Press, Oxford, GB, vol. 13, No. 8-9, Oct. 1, 2003, pp. 957-979.
Billinghurst, Real World Teleconferencing, pp. 1-5.
Anupam, et al., Collaborative Multimedia Scientific Design in SHASTRA, Department of Computer Sciences, Purdue University, West Lafayette, Indiana, 12 pgs.
Alex T. Pang et al., "Approaches to Uncertainty Visualization", The Visual Computer, vol. 13, No. 8, Nov. 18, 1997, pp. 370-390.
Akatsuka et al. "Compensation for End to End Delays in a VR System." Proceedings of IEEE Virtual Reality Annual International Symposium, Mar. 1998, pp. 156-159.
Gibson, et al. "Simulating surgery using volumetric object representations, real-time volume rendering and haptic feedback," Mitsubishi Research Laboratories, pp. 1-21 (1997).

* cited by examiner

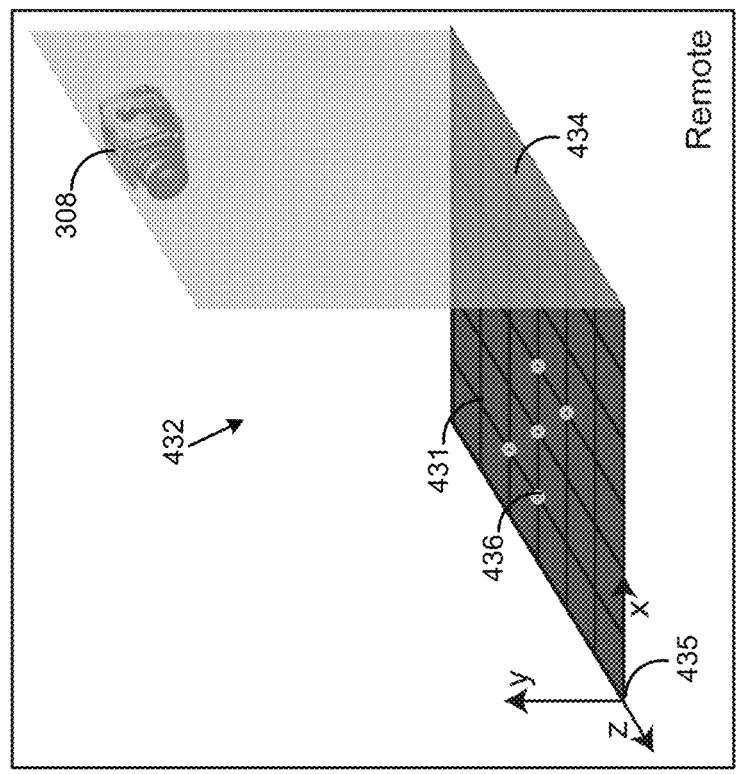
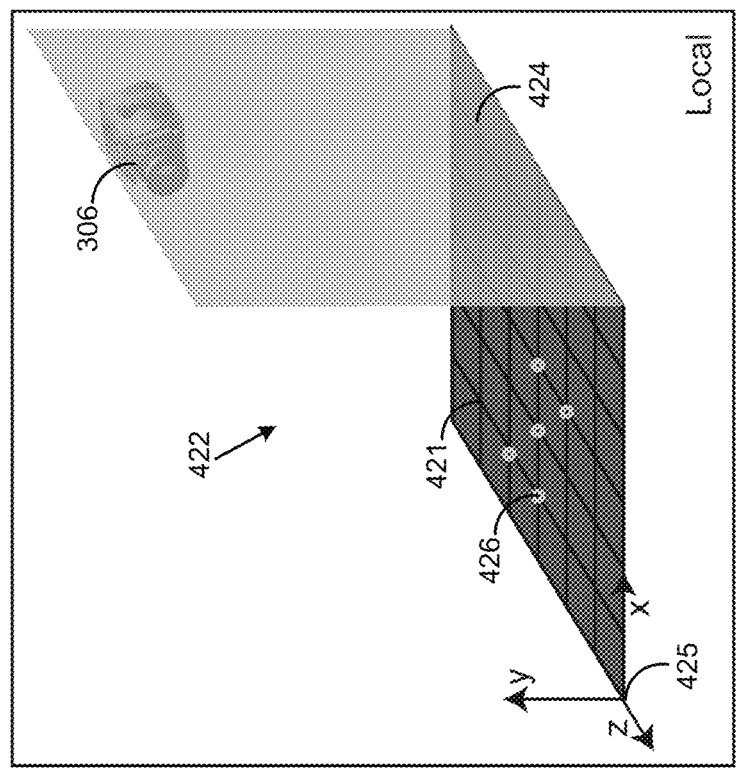
FIG. 4B

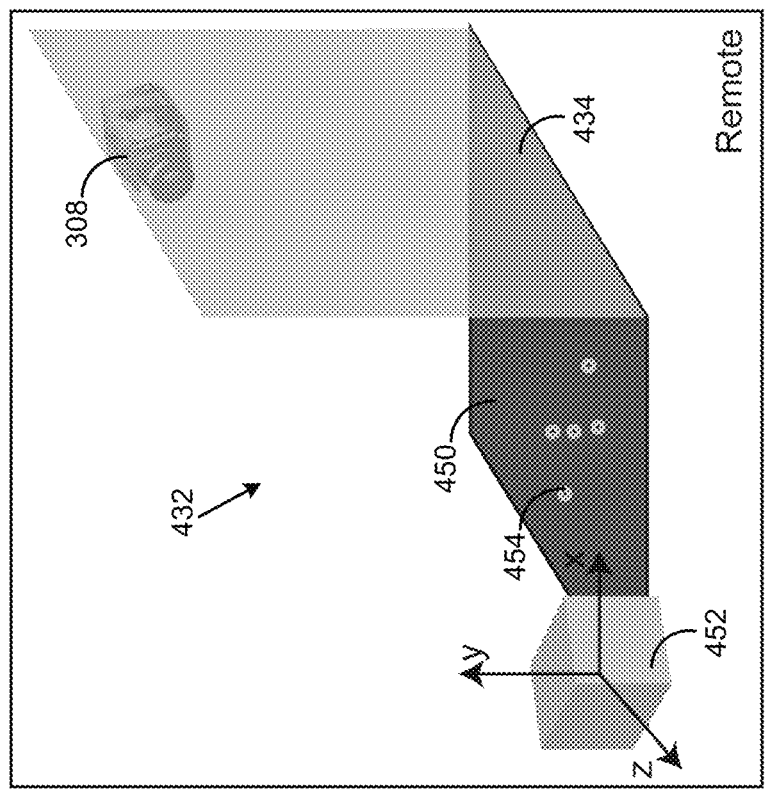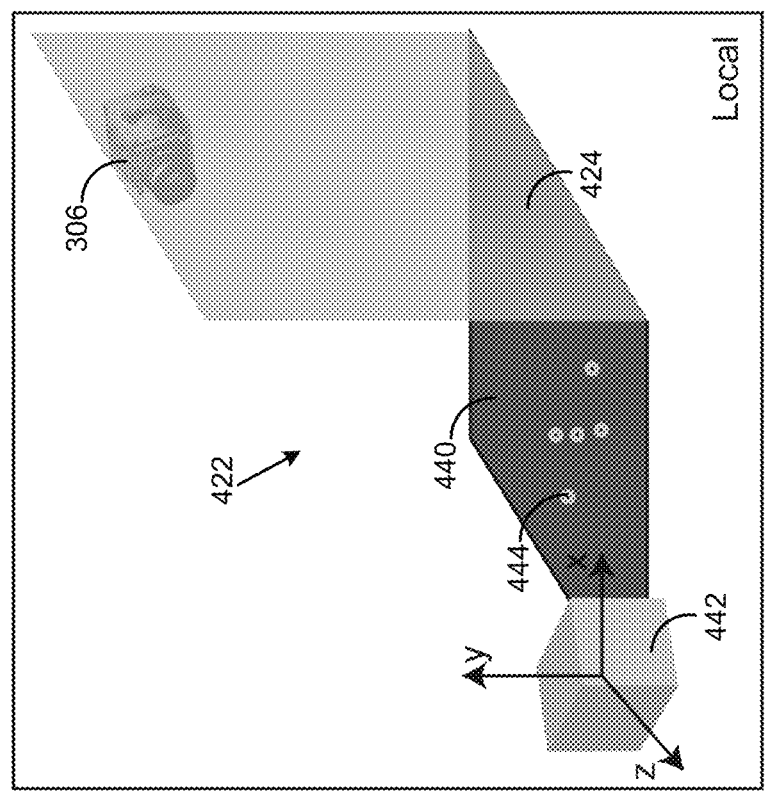
FIG. 4C

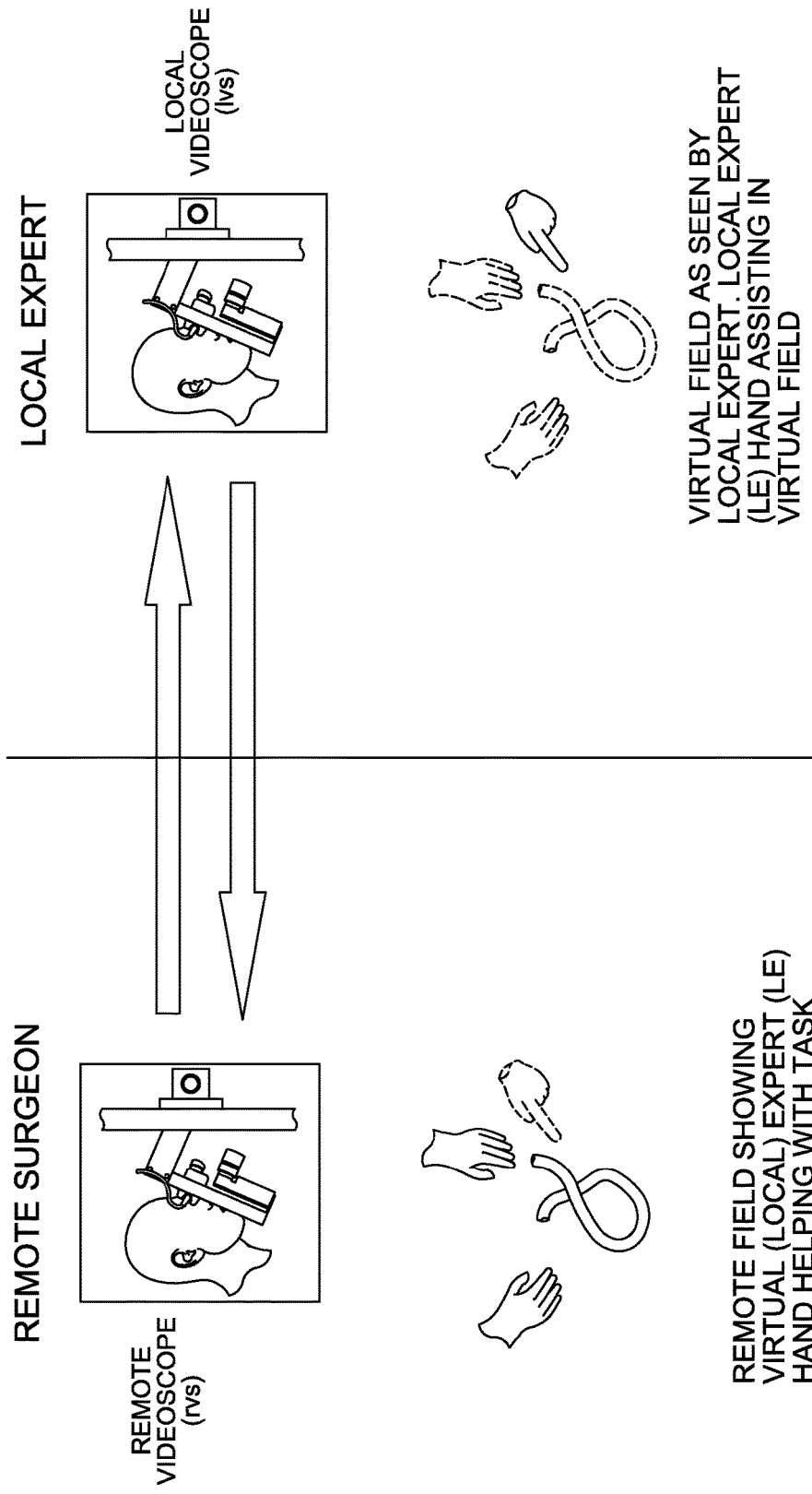

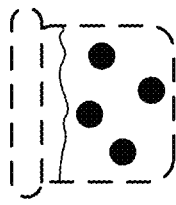

Slices of MRI scan of beaker of object.

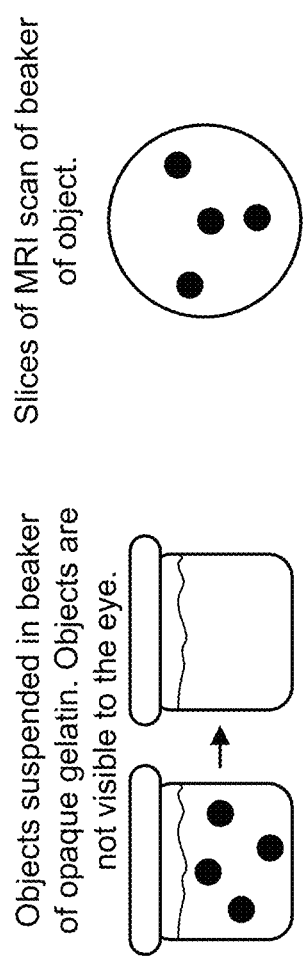

Objects suspended in beaker of opaque gelatin. Objects are not visible to the eye.

Computer volume rendering of "virtual beaker."

Real and virtual beaker as viewed through a videoscope.

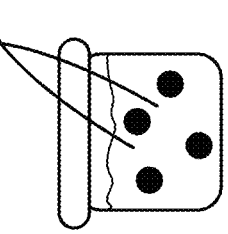

User interface within the videoscope enables user to scale/rotate virtual beaker so that it is superimposed onto real beaker.

Once merged, the user can use the virtual beaker to navigate within the real beaker.

FIG. 14

SYSTEM AND METHOD FOR IMAGE REGISTRATION OF MULTIPLE VIDEO STREAMS

FEDERAL GOVERNMENT SUPPORT CLAUSE

The present invention was developed with Government funds provided by the Department of Energy under Grant/Contract numbers H30912, H34612, and H35662. The Government has certain rights in this invention.

BACKGROUND

Video combiners in extensive use today combine video from two separate sources using various multiplexing and media combining technology. When two video sources are combined or multiplexed the two video sources are not necessarily in a desired alignment. Misalignments are often due to lack of synchronization between the video sources.

As an example, conventional video streaming rely on algorithms to systematically remove data during compression and decompression processes that allow more efficient transmission of video/image feeds. Loss of data and changes of resolution, aspect ration, skew, and other factors impact (e.g. transform) the raw viewing of video. Accordingly, when two video streams are combined from two distinct sources, the resultant composite video or series of images can be misaligned.

SUMMARY

Disclosed are systems and methods for establishing image registration of multiple video/image streams to align multiple video/image streams for a desired rendering of images. A Spatial Image Registration System (SIRS) uses detection methods, systems, symbols and/or detection points introduced within the images of separate video feeds to verify and if necessary, apply multiple image transformations to perform an alignment between the original and transmitted feeds. In the case of virtual interactive presence (VIP), SIRS aides in creating a common field of interest with users interactions spatially registered or matched regardless of transmission or display differences.

Methods are described for image registration or co-localization. One method comprises: rendering a common field of interest that reflects a presence of a plurality of elements, wherein at least one of the elements is a remote element located remotely from another of the elements; and updating the common field of interest such that the presence of the at least one of the elements is registered relative to another of the elements.

Another method comprises: generating a first image representing a first element; generating a second image representing a second element disposed remotely from the first element; and rendering a composite image including the first image and the second image, wherein at least one of the first image and the second image is registered relative to the other of the first image and the second image based upon a registration feature.

A system for image registration is described. The system comprises: a display configured for displaying a common field of interest; a sensor configured for obtaining image data; a processor in signal communication with the display and the sensor, wherein the processor is configured to perform steps comprising, rendering a common field of interest that reflects a presence of a plurality of elements based upon the image data, wherein at least one of the elements is a remote element located remotely from another of the elements; updating the common field of interest such that the presence of the at least one of the elements is registered relative to another of the elements; and outputting the common field of interest to the display.

Additional advantages will be set forth in part in the description which follows or may be learned by practice. The advantages will be realized and attained by means of the elements and combinations particularly pointed out in the appended inventive concepts. It is to be understood that both the foregoing general description and the following detailed description are exemplary and explanatory only and are not to be considered restrictive.

BRIEF DESCRIPTION OF THE DRAWINGS

The accompanying drawings, which are incorporated in and constitute a part of this specification, illustrate embodiments and together with the description, serve to explain the principles of the methods and systems provided:

FIG. 4B illustrates a local field and a remote field of an exemplary process performed by the registration system of FIG. 3;
FIG. 4C illustrates a local field and a remote filed of an exemplary process performed by the registration system of FIG. 3;
FIG. 13 illustrates virtual presence in a remote surgical environment;
FIG. 14 illustrates merging of medical imaging with an operative field.

DETAILED DESCRIPTION

Figure 1:
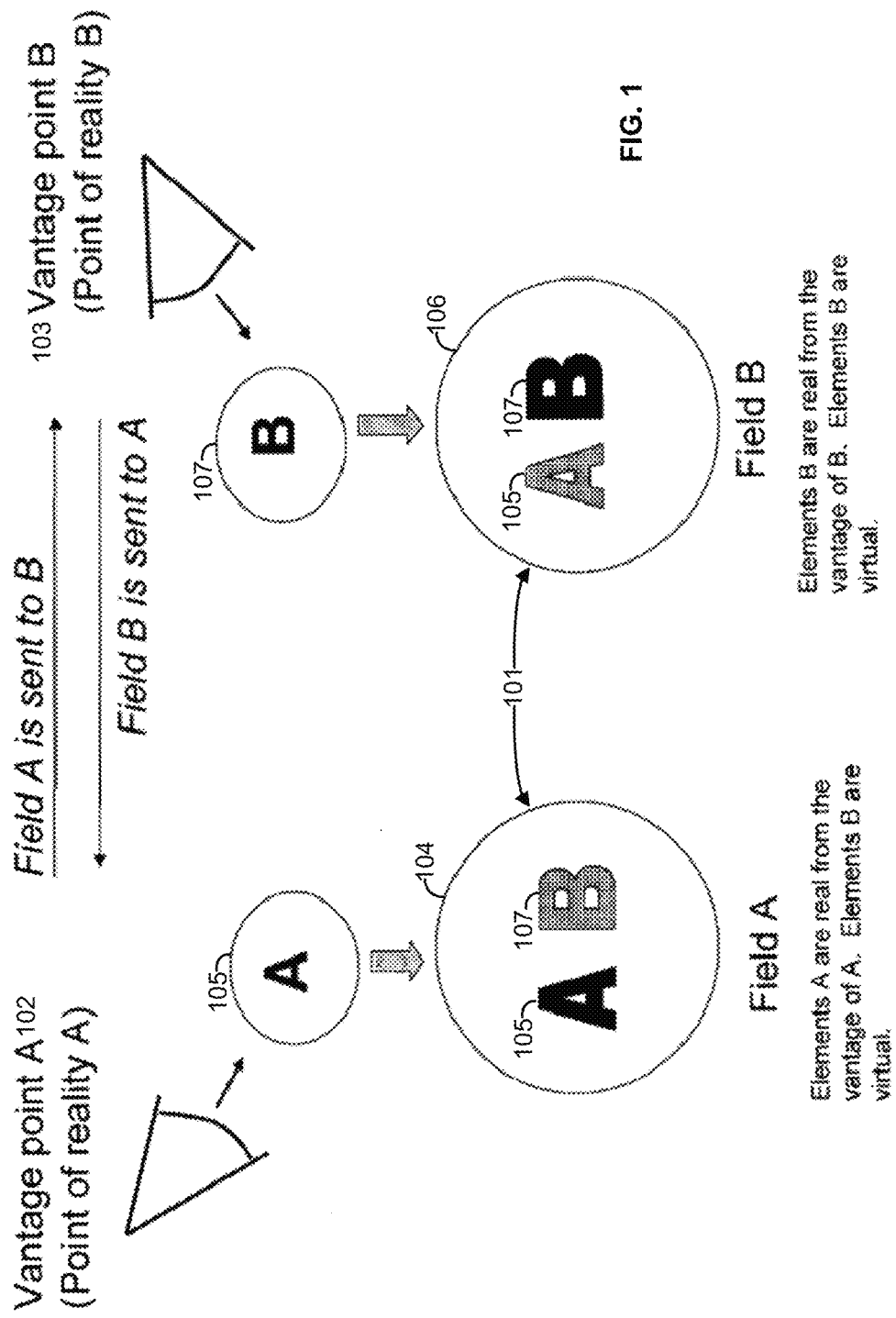
FIG. 1 illustrates virtual interactive presence.

Before the present methods and systems are disclosed and described, it is to be understood that the methods and systems are not limited to specific synthetic methods, specific components, or to particular compositions, as such may, of course, vary. It is also to be understood that the terminology used herein is for the purpose of describing particular embodiments only and is not intended to be limiting.

As used in the specification and the appended inventive concepts, the singular forms "a," "an" and "the" include plural referents unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

Disclosed are methods and systems for image registration of multiple video streams. The disclosed methods and systems can utilize virtual reality. Virtual reality (VR) refers to a computer-based application which provides a human-computer interface such that the computer and its devices create a sensory environment which is dynamically controlled by the actions of the individual, so that the environment appears "real" to the user. With VR, there is communication between a computer system and a user. The computer creates a sensory environment for the user to experience which may be, in one aspect, multisensory (although this is not essential) and the computer creates a sense of reality in response to user inputs.

In one exemplary aspect, the system disclosed can utilize at least two types of VR, Immersive and Non-immersive. Immersive VR creates the illusion that the user is actually in a different environment. In one aspect, the system accomplishes this through the use of such devices as Head Mounted Displays (HMD's), earphones, and input devices such as gloves or wands. In another aspect, in order to enhance to realism of the experience, a plurality of Degrees of Freedom (DOF's) are utilized, which the software can simulate. Generally, the more the DOF's, the better the realism of the experience. Exemplary DOF's include, without limitation: X,Y,Z, roll, pitch, and yaw.

Non-immersive VR creates an environment that is differentiable from the user's surrounding environment. It does not give the illusion that the user is transported to another world. Non-immersive VR works by creating a 3-dimensional image and surround sound through the use of stereo projection systems, computer monitors, and/or stereo speakers. Non-immersive VR can be run from a personal computer without added hardware.

In one aspect, movement in Immersive VR can be realized by a system through the use of optical, acoustical, magnetic, or mechanical hardware called trackers. Preferably, the input devices have as many of these trackers as possible, so that movement can be more accurately represented. For instance, virtual gloves can have up to 3 trackers for each index, and more for the palm and wrist, so that the user can grab and press objects. In one aspect, the trackers can be equipped with positioning sensors, that tell a computer which direction the input is facing and how the input device is tilted in all directions. This gives a sensor with six degrees of freedom.

Output devices bring the user to the virtual world. An example of an output device that can be used in the present system include, without limitation, head mounted displays (HMD) in the form of glasses or goggles, which allow a user to wear a display system on their head. One approach to the HMD is to use a single Liquid Crystal Display (LCD), wide enough to cover both eyes. Another approach is to have two separated displays—one for each eye. This takes somewhat more computer power, since the images displayed are different. Each display has a separate image rendered from the correct angle in the environment. Eye-tracking can be combined with HMDs. This can allow, for example, surgeons to move their eyes to the part of an image they want to enhance.

Another example of an output device that can be used in an embodiment of the present system is shuttered glasses. This device updates an image to each eye every other frame, with the shutter closed on the other eye. Shuttered glasses require a very high frame rate in order to keep the images from flickering. This device is used for stereo monitors, and gives an accurate 3-d representation of a 2-d object, but does not immerse the user in the virtual world.

Another output device that can be used in an embodiment of the present system is a screen with multiple projectors. The screen can be either a plane or bent. A challenge when using multiple projectors on the same screen is that there can be visible edges between the projections. This can be remedied by using a soft-edge system wherein the projection goes more and more transparent at the edges and the projections overlap. This produces an almost perfect transition between the images. In order to achieve a desired 3D effect, shuttered glasses can be used. Special glasses can be used, that alternate between making the glass either completely opaque or completely transparent. When the left eye is opaque, the right one is transparent. This is synchronized to the projectors that are projecting corresponding images on the screen.

In another aspect, a Cave Automatic Virtual Environment (CAVE) can also be used in the present system. A CAVE can use mirrors in a cube-shaped room to project stereo images onto the walls, giving the illusion that you are standing in a virtual world. The world is constantly updated using trackers, and the user is allowed to move around almost completely uninhibited.

Disclosed are methods and systems for image registration. Such methods and systems can render a number of elements/participants virtually present into a field of interest in a manner such that the users can interact for any given purpose, such as the delivery of remote expertise. A field of interest can comprise varying amounts of "real" and "virtual" elements, depending on a point of view. Elements can include any "real" or "virtual" object, subject, participant, or image representation. Various components of the disclosed methods and systems are illustrated in FIG. 1.

A common field of interest 101 can be a field within which elements are physically and/or virtually present. Point of Reality (or Point of View) can refer to the vantage of the element/participant that is experiencing the common field of interest. In FIG. 1, exemplary points of reality, or points of view, are shown at 102 and 103, representing displays. The common field of interest 101 can appear similar from both vantages, or points of view, but each comprises differing combinations of local (physical) and remote (virtual) elements/participants.

Local elements can be elements and/or participants which are physically present in the common field of interest. In FIG. 1, element A 105 is a local element for field A 104 and is physically present in field A 104. Element B 107 is a local element for field B 106 and is physically present in field B 106. It is understood that virtual elements (not shown) can be inserted or overlaid in field A 104 and/or field B 106, as desired.

Remote elements can be elements and/or participants that are not physically present in the common field of interest. They are experienced as "virtually present" from any other local vantage point. As shown in FIG. 1, element B 107 is a remote element to field A 104 and is virtually present in field A 104. Element A 105 is a remote element in field B 106 and is virtually present in field B 106.

Figure 2A:
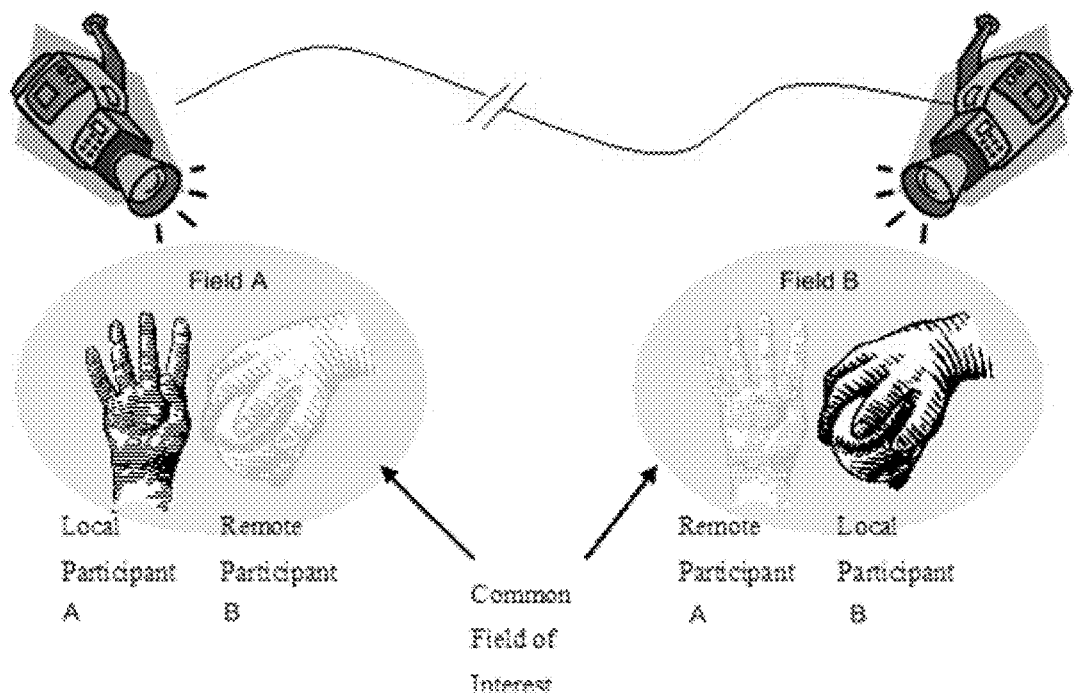
FIG. 2A illustrates virtual interactive presence.

Methods for rendering a virtual interactive presence by combining local and remote elements and/or participants can comprise one or more of the following steps. A common local field can be rendered in a manner that reflects the presence of the field, elements and/or participants. As shown in FIG. 2A, Participant A can experience real elements in field A through a viewer. The common local field can be rendered such that it is experienced remotely in a manner that enables remote participants to experience it similarly to the local persons. As shown in FIG. 2A, this is illustrated by Participant A experiencing element B as virtually present in field A.

Remote persons can insert themselves and/or interact with the virtual field as rendered to them. For example, Participant A can insert hands, instruments, etc. into field A and interact with the virtual element(s) B. Viewer B can view a 'virtual compliment' to this, with Viewer B's real elements interacting with Participant A's virtual elements.

The common local field can be continuously updated such that the presence of the remote participants can be rendered in real time. For example, the remote scene can be the most up-to-date available with the time lag between the remote capture and the local render kept as low as possible. Conversely, if there is a need to introduce a timing difference, this can be accomplished as well.

The common local field can be scaled to a size and depth to meaningfully match the local scene. And the common local field can be configurable, such that remote elements can be made more or less transparent, removed entirely, or otherwise altered to suit the needs of the local user.

Each field is captured by a digital camera. The resulting image is physically distorted from its reality, based upon the physical characteristics of the camera. A processor, therefore, receives and displays a "physically" distorted version of the local reality. Likewise, a digital camera also captures the remote field(s), but the incoming stream is relayed through a transmission device and across a network. The processor, therefore, receives the remote stream that contains both physical and transmission-based distortion. The processor must then apply a series of transformations that removes the physical and transmission-based distortion from the common local field.

Figure 2B:
FIG. 2B illustrates a local expert assisting a remote user.

The local participants can experience the virtually present participants in a manner that enables continuous interaction in the common local field. FIG. 2B illustrates a local expert assisting a remote user. The hands of the local expert 201 are slightly transparent and superimposed into the field that is viewed by the remote user. The remote user can view the local expert's hands, the remote user's hands and a puzzle located at the remote user's location. The local expert is assisting the remote user in assembling a puzzle.

Figure 3:
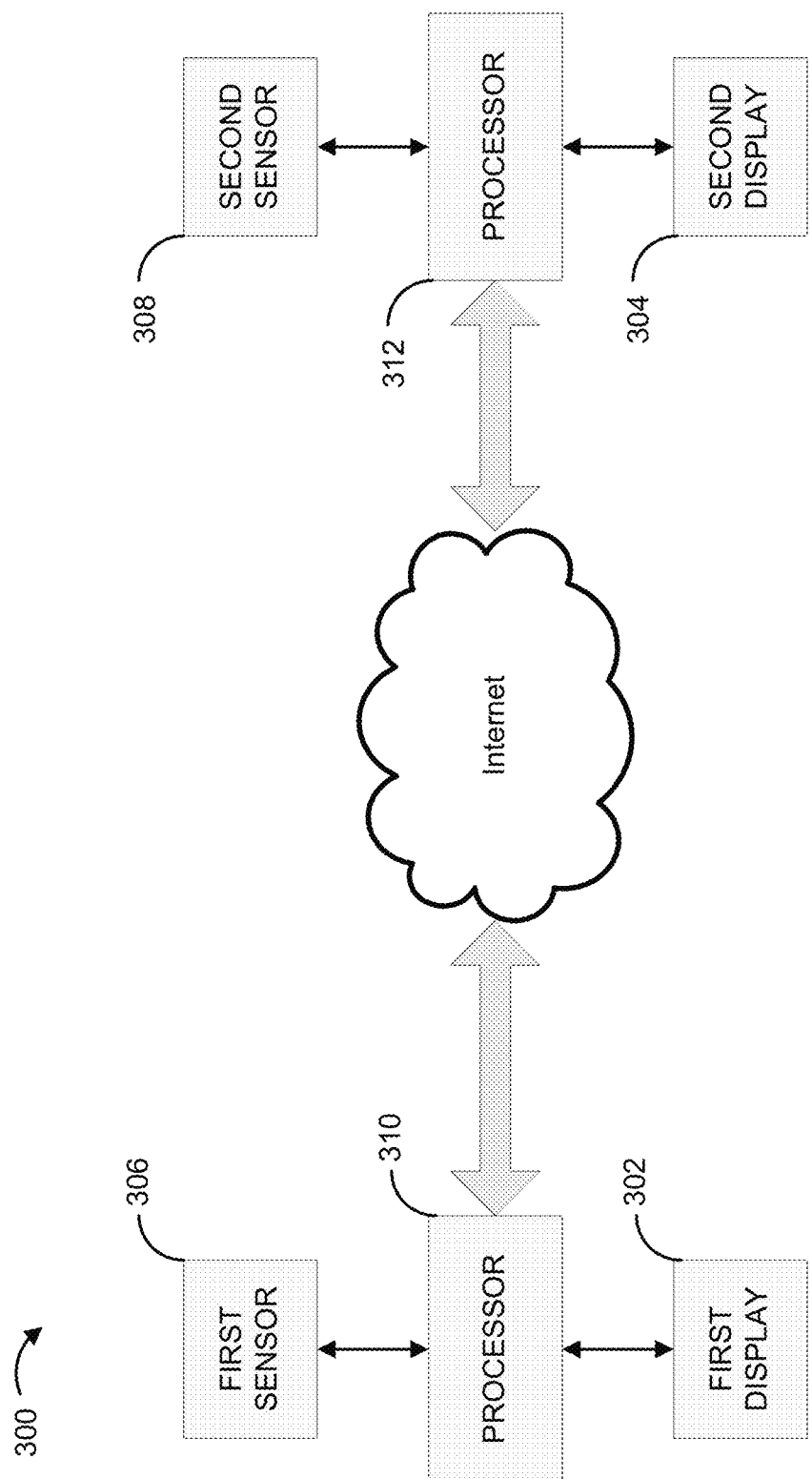
FIG. 3 illustrates an exemplary registration system.

FIG. 3 illustrates an exemplary registration system 300. As shown, the registration system 300 can comprise a first display 302 and a second display 304 configured for displaying one or more of an image, a video, a composite video/image, and a common field of interest, for example. However, it is understood that any number of displays can be included in the system 300. In certain aspects, the second display 304 can be disposed remotely from the first display 302. As an example, each of the first display 302 and the second display 304 can be configured to render the common field of interest thereon. As a further example, each of the first display 302 and the second display 304 can be configured to render at least one of the local field and the remote field thereon. In certain aspects, at least one of the first display 302 and the second display 304 can be a VIP display, as described in further detail herein. However, it is understood that each of the first display 302 and the second display 304 can be any type of display including a monoscopic display and a stereoscopic display, for example. It is understood that any number of any type of display can be used.

A first sensor 306 can be in signal communication with at least the first display 302 and can be configured for obtaining image data such as a virtual presence data, for example. In certain aspects, the first sensor 306 can be one or more of a camera, an infrared sensor, a light sensor, a RADAR device, a SONAR device, a depth scan sensor, and the like. It is understood that the first sensor 306 can be any device or system capable of capturing/obtaining an image data representative of at least one of a "real" element" and a "virtual" element.

A second sensor 308 can be in signal communication with at least the second display 304 and can be configured for obtaining image data such as virtual presence data, for example. In certain aspects, the second sensor 308 can be one or more of a camera, an infrared sensor, a light sensor, a RADAR device, a SONAR device, a depth scan sensor, and the like. It is understood that the second sensor 308 can be any device or system capable of capturing/obtaining an image data representative of at least one of a "real" element" and a "virtual" element. It is further understood that any number of sensors can be used.

A plurality of processors 310, 312 can be in direct or indirect signal communication with at least one of the first display 302, the second display 304, the first sensor 306, and the second sensor 308. Each of the processors 310, 312 can be configured to render the image data collected by the sensors 306, 308 onto at least one of the displays 302, 304. It is understood that the processors 310, 312 can be configured to modify the image data and the resultant image for transmission and display. It is further understood that any number of processors can be used, including one. In certain aspects, the system 300 comprises only the processor 310, 312 in data communication with each other.

In certain aspects, each of the displays 302, 304 can comprise an associated one of the processors 310, 312 for rendering images onto the displays 302, 304. Each of the processors 310, 312, or another system comprising a processor, can communicate with each other through a network connection. For example, remote sites can connect via the Internet. Tasks can be divided amongst each of the processors 310, 312. For example, one of the processors 310, 312 can be configured as a graphics processor or graphics server and can gather images from one of the sensors 306, 308 and/or a network server, perform an image composition tasks, and drive one or more of the displays 302, 304.

Figure 4A:
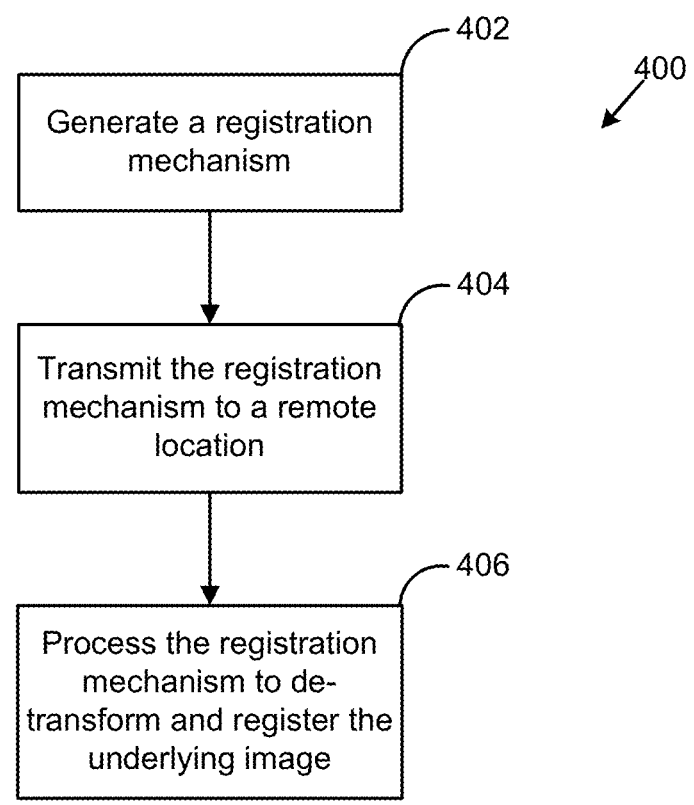
FIG. 4A illustrates an exemplary process performed by the registration system of FIG. 3.

FIG. 4A illustrates exemplary processes 400 that can be performed with at least one the processors 310, 312. As shown, the processors 310, 312 can be configured to render a common field of interest that reflects a presence of a plurality of elements based upon the image data obtained by at least one of the sensors 306, 308. As an example, at least one of the elements rendered in the common field of interest can be a remote element physically located remotely from another of the elements. In certain aspects the processors 310, 312 can be configured to update the common field of interest such that the presence of at least one of the elements is registered relative to another of the elements. The processors 310, 312 can also be configured to render/output the common field of interest to at least one of the displays 302, 304. As an example, the processors 310, 312 can render interaction between a remote user and a local user in the common field of interest. As a further example the presence of the remote element can be rendered in real time to the local user and the presence of a local element can be rendered in real time to the remote user.

In step 402, a registration mechanism can be generated. As an example, the registration mechanism can be an image including a registration feature having a pre-determined location and arrangement. In an aspect, at least one of the first sensor 306 and the second sensor 308 can capture image data to generate a registration image representing the registration mechanism. As an example, a pre-defined pattern of dots or markers having any shape and size can be digitally inserted into the registration image to define the registration feature. As a further example, the registration feature can be a virtual image overlaid or combined with the registration image.

An exemplary case is shown in FIG. 4B, wherein the sensors 306, 308 capture image data to produce a registration mechanism. As illustrated in FIG. 4B, each of a pair of coordinate systems 421, 431 with identical dimensions is disposed in each of a local field 422 and a remote field 432. As an example, each of the coordinate systems 421, 431 can be a square grid system. However, other coordinate systems can be used. The coordinate systems 421, 431 are situated identically in position and orientation relative to the respective sensors 306, 308 in each of the respective fields 422, 432. In an aspect, mounts 424, 434 coupled to the sensors 306, 308 are perpendicular to an edge of the respective coordinate system 421, 431. A fiducial 425, 435 or reference point can be defined in substantially identical or identical pre-determined locations in each of the fields 422, 432 based upon the coordinate systems 421, 431, such as a corner of a lower-left quadrant, for example.

In an aspect, a pre-defined first pattern of dots 426 or markers can be disposed on the coordinate system 421 as a registration feature, and the coordinates of each of the dots 426 with respect to the fiducial 425 can be stored. A second pattern of dots 436 or markers can be disposed on the coordinate system 431 with respect to the fiducial 435 so that a coordinate of each of the dots 436 of the second pattern corresponds to a coordinate of one of the dots 426 of the first pattern. Image data of the field 422 captured by the sensor 306 can be defined as the registration mechanism including the dots 426 as the registration feature. As an example, data relating to the coordinates of each of the dots 426, 436 can be stored on a storage device for subsequent retrieval. As a further example, the data relating to the coordinate of each of the dots 426, 436 can be transmitted between the processors 310, 312 of the system 300 to calibrate each of the fields 422, 432.

In an exemplary aspect, illustrated in FIG. 4C, a spatial tracking, motion tracking, or similar system can be used in lieu of a grid. As an example, in FIG. 4C, a Flock of Birds (Ascension Technology Corp., Burlington, Vt.) motion tracking system is used. However, other spatial tracking and/or motion tracking systems can be used. As shown in FIG. 4C, a plurality of planes 440, 450 with identical dimensions can be positioned in each field 422, 432. The planes 440, 450 can be arranged to define a bottom of the respective fields 422, 432. As an example, the planes 440, 450 can be situated identically in position and orientation with respect to the sensors 306, 308 in each of the fields 422, 432. In an aspect, mounts 424, 434 coupled to the sensors 306, 308 can be perpendicular to an edge of the respective plane 440, 450. A fiducial 442, 452 or reference point can be recognized in identical pre-determined locations of each of the fields 422, 432 such as a corner of a lower-left quadrant, for example.

As an example, shown in FIG. 4C, the fiducials 442, 452 are devices that are configured to transmit a pulsed DC magnetic field. As a further example, a pre-defined first pattern of dots 444 or markers can be disposed on the plane 440 as a registration feature. The coordinates of each of the dots 444 with respect to the fiducial 442 can be noted by affixing magnetic receivers (not shown) to each of the dots 444 to measure the magnetic field produced by the fiducial 442 at the various locations of the dots 444. From the measurements, the position and coordinates of each of the dots 444 relative to the fiducial 442 can be computationally derived by the Flock of Birds system and stored. As an example, data relating to the coordinates of each of the dots 444 can be stored on a storage device for subsequent retrieval. As a further example, the data relating to the coordinate of each of the dots 444 can be transmitted between the processors 310, 312 of the system 300 to calibrate each of the fields 422, 432.

A second pattern of dots 454 or markers can be disposed on the plane 450 with respect to the fiducial 452 and based upon the position and coordinates of each of the dots 444 relative to the fiducial 442. Accordingly, a coordinate of each of the dots 454 of the second pattern can correspond to a coordinate of one of the dots 444 of the first pattern, relative to the respective fiducial 442, 452. It is understood that the position and coordinate information relating to the dots 444, 454 can be transmitted between the fields 422, 432 or processor 310, 312 by a system external to the system 300. It is further understood that the position and coordinate information relating to the dots 444, 454 can be transmitted along with image data. Other methods for generating a registration mechanism can be used Returning to FIG. 4A, the registration mechanism having the registration feature is transmitted to one of the processors 310, 312 for transformation and rendering, as shown in step 404. During the transmission of the registration mechanism, the underlying data can be compressed and decompressed and may be modified or lost. Accordingly, when the registration mechanism is received and rendered by the one of the processors 310, 312, the elements represented in the registration mechanism may be skewed, shifted, cropped, or transformed. Likewise, the registration feature would also be transformed in a similar manner, whereby the resultant pattern and location of the registration feature would not match the pre-defined location and pattern prior to transmission.

Figure 4D:
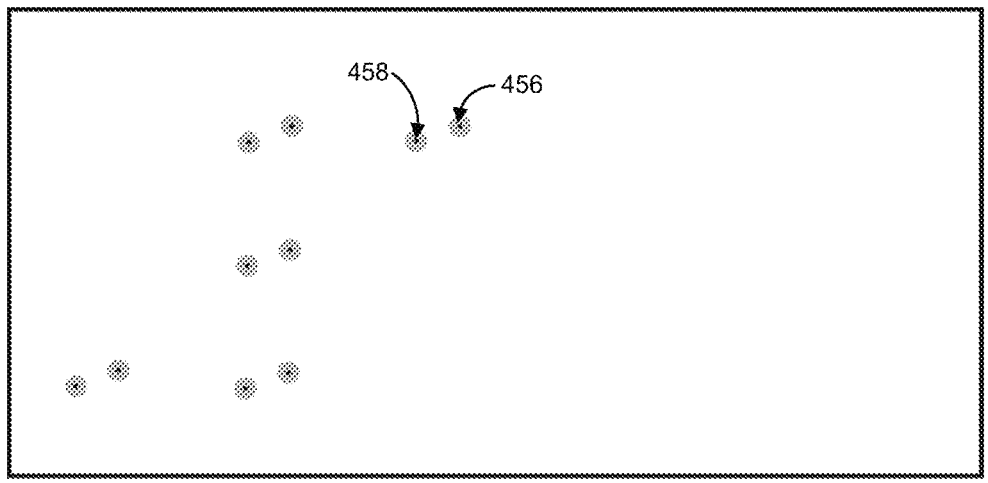
FIG. 4D illustrates an offset of a registration mechanism.

In step 406, the one of the processors 310, 312 receives the registration mechanism to de-transform or register the elements represented thereby. As an example, the one of the processor 310, 312 analyzes the registration mechanism to discover a location and arrangement of the registration feature. Since the registration feature has pre-determined characteristics such as location and arrangement, one or more of the processors 310, 312 can compare the current transformed location and arrangement to the known, pre-determined location and arrangement. As an illustrative example, FIG. 4D shows the registration feature in an offset position 456 due to transformations caused form transmitting the registration mechanism. Accordingly, one or more of the processors 310, 312 can compare the offset position 456 of the registration feature to an known, original position 458.

Figure 4E:
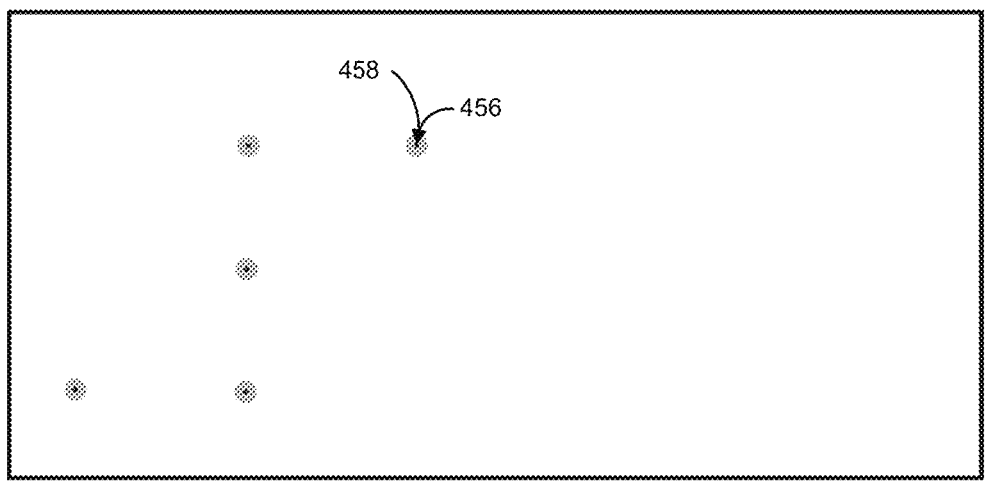
FIG. 4E illustrates the transformation of the offset of the registration mechanism of FIG. 4D.

From the comparison, the one of the processors 310, 312 can determine a set of transforms that should be applied to the registration mechanism in order to return the underlying data or image to the desired state (e.g. the original position 458), as shown in FIG. 4E. One skilled in the art of image processing would understand that various transform methods and algorithms can be applied to an image to "de-transform" the image to an original state. One or more of the processors 310, 312 can continue to apply transforms to the registration mechanism until the original arrangement and location of the registration features are achieved, as shown in FIG. 4E.

Figure 4F:
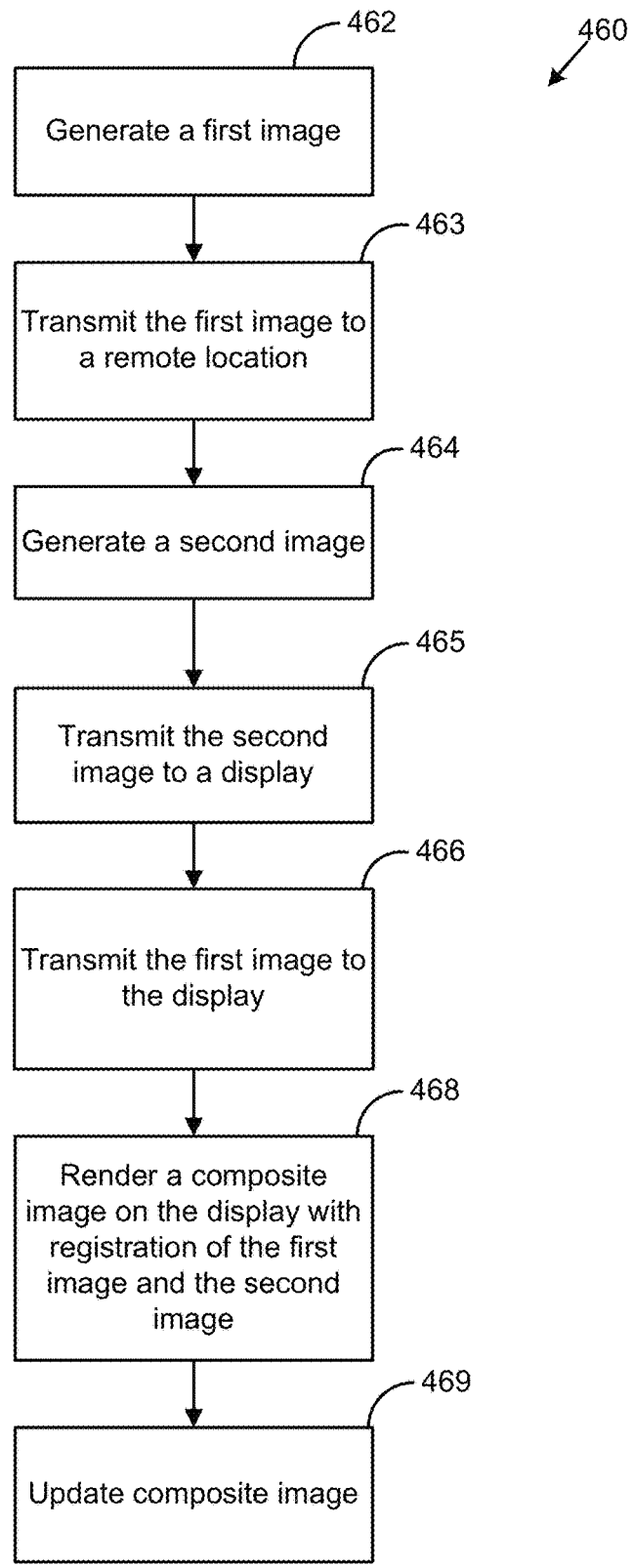
FIG. 4F illustrates an exemplary process performed by the registration system of FIG. 3.

FIG. 4F illustrates an exemplary process 460 that can be performed with the system 300. In step 462, the first sensor 306 can capture image data to generate a first image representing a first element. Alternatively, the first image can be generated from stored image data or the like. As an example, the first image can comprise a registration feature having a pre-determined location and arrangement relative to the first image. In certain aspects, the registration feature can be inserted into the first image as a detectable marker. For example, a pre-defined pattern of dots can be digitally inserted into the image. As a further example, the registration feature can be a virtual image overlaid or combined with the first image. However, any registration feature or mechanism can be used.

The first image comprising the registration feature can be transmitted to the remote processor 312 for transformation and rendering, at step 463. During the transmission of the first image, the underlying data can be compressed and decompressed and may be modified or lost. Accordingly, when the first image is received and rendered by the processor 312, the elements represented in the first image may be skewed, shifted, cropped, or transformed. Likewise, the registration feature would also be transformed in a manner similar to the first image, whereby the resultant pattern and location of the registration feature would not match the pre-defined location and pattern prior to transmission.

In step 464, the second sensor 308 can capture image data to generate a second image representing a second element disposed remotely from the first element. It is understood that the second image can be generated from stored image data or the like. As an example, the second image comprises a registration feature having a pre-determined location and arrangement relative to the second image. In certain aspects, the registration feature can be inserted into the second image as a detectable marker. For example, a pre-defined pattern of dots can be digitally inserted into the image. As a further example, the registration feature can be a virtual image overlaid or combined with the second image.

In step 465, the second image having the registration feature can be transmitted to the second display 304 disposed locally relative to the second sensor 308. During the transmission of the second image, the underlying data can be altered for formatting and compatibility with the second display 304. Accordingly, when the second image is received and rendered onto the second display 304, the elements represented in the second image may be skewed, shifted, cropped, or transformed. Likewise, the registration feature would also be transformed in a manner similar to the first image, whereby the resultant pattern and location of the registration feature would not match the pre-defined location and pattern prior to transmission. Following this transmission, the second image rendered on the second display 304 can be analyzed by processor 312 to determine the transformation of the second image.

In step 466, the processor 312 transmits the first image onto the second display 304 for rendering thereon. Similar to the rendering of the second image, a transformation may occur when rendering the first image to the second display 304. As such, each of the first image and the second image may be transformed or altered from intended previous state prior to transmission and rendering. Following this transmission, the first image rendered on the second display 304 can be analyzed by processor 312 to determine the transformation of the second image.

In an aspect, where transform parameters are known based upon the components and equipment being used, the processors 310, 312 can retrieve the known transform parameters and automatically calculate reverse transforms in order to return the images to an original state. As an example, data relating to known transforms for particular equipment and components can be stored and processed using a priori algorithms and methods. However, other methods can be used.

In step 468, the processor 312 can render a composite image to the second display 304 including the first image and the second image wherein each of the first image and the second image can be registered relative to the other of the first image and the second image based upon the registration feature. As an example, the processor 312 analyzes each of the first image and the second image to discover a location and arrangement of the registration feature for each of the first image and the second image. Since the registration feature for each of the first image and the second image have known, pre-determined characteristics such as location and arrangement, the processor 312 can compare the current transformed location and arrangement to the known, pre-determined location and arrangement. From the comparison, the processor 312 can determine a set of transforms that should be applied to each of the first image and the second image in order to return the first image and the second image to a desired state. One skilled in the art of image processing would understand that various transform methods and algorithms can be applied to an image to "de-transform" the image to an original state. The processor 312 can continue to apply transforms to at least one of the first image and the second image until the original arrangement and location of the registration features is achieved.

In an aspect, the registration feature of the second image can be used as a local reference to which the registration feature of the first image can be registered and aligned. As an example, the processor 312 can locate a centroid of each of the elements of the registration features for the first image and the second image. As a further example, the first image can be linearly shifted along any number of dimensional axes to align the first image to the second image. It is understood that non-linear shifting and alignment techniques can also be applied. It is further understood that the first image can be padded or cropped in order to match the boundaries of the second image (or some other reference image).

It is understood that the second image can be transmitted to the first display and combined in a similar manner to generate a composite image on the first display. In this way, the first display 302 and the second display 304 render composite images representing the same alignment of the first image and the second image relative to each other. Accordingly, a viewer of the second display 304 is assured that the first image received from a remote location is rendered in an intended orientation and alignment relative to the second image. Likewise, a viewer of the first display 302 is assured that the second image received from a remote location is rendered in an intended orientation and alignment relative to the first image that is generated local to the first display 302.

In step 469, the composite image rendered on each of the first display and the second display can be updated to reflect any changes to the first image and/or the second image. For example, where the sensors 306, 308 are video cameras, each sequentially captured video frame can represent a modified version of the first image and the second image, respectively. Accordingly, as the first image and the second image are modified, the composite image can be updated and each of the modified first image and the modified second image can be registered and aligned for rendering on the displays 302, 304. It is understood that any number of images and displays can be aligned in a similar manner as described herein.

Figure 5:
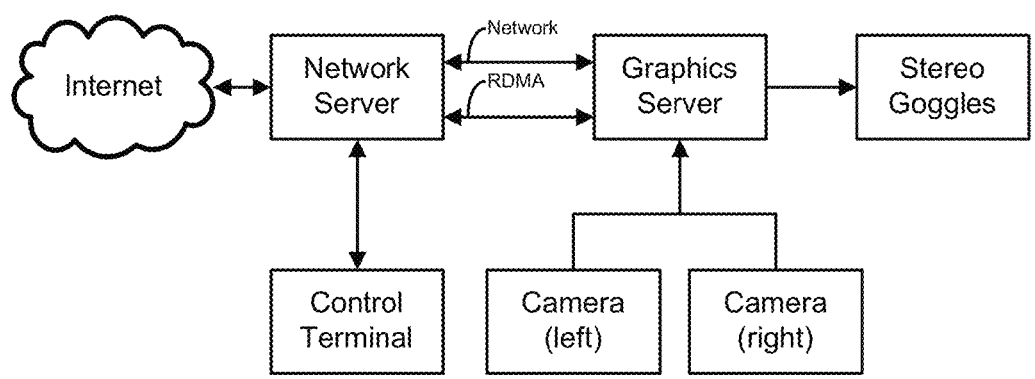
FIG. 5 illustrates an exemplary virtual presence system.

FIG. 5 illustrates an exemplary virtual presence system. One such system can be used by each remote participant that is to join the same session. Each system can communicate with each other through a network connection. For example, remote sites can connect via the internet. Tasks can be divided amongst a plurality of computers in each system. For example, one computer (a graphics server) can gather images from local cameras and a network server, perform the stereo image composition tasks, and drive a local stereoscopic display system. As a further example, the processor(s) 310 of system 300 can be embodied by the graphics server.

Figure 6:
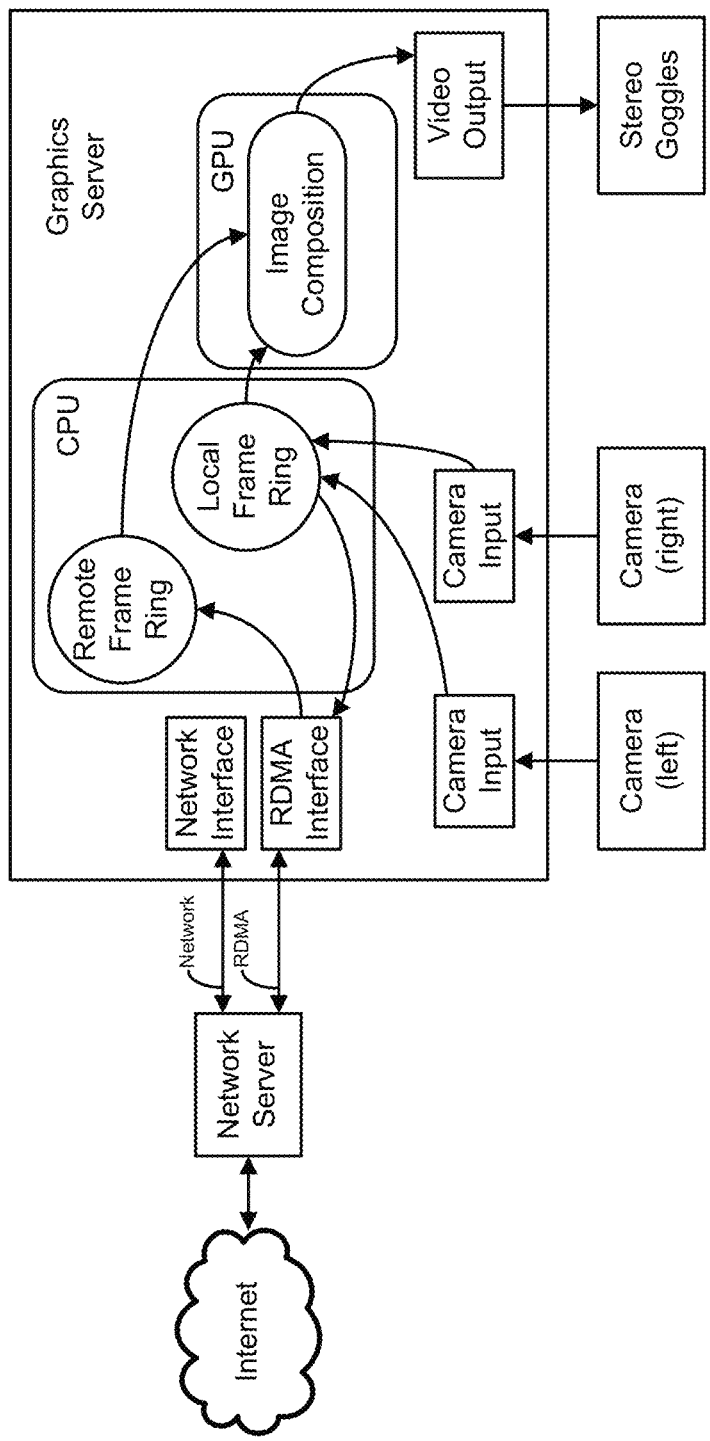
FIG. 6 illustrates exemplary processes performed within a graphics server.

FIG. 6 illustrates exemplary processes that can be performed with the graphics server. Images can be gathered into local data structures (frame rings). Local images can be gathered from a plurality of cameras, for example two cameras. Remote images can be provided by the network server via a high-speed remote direct memory access (RDMA) connection, for example. These images can be combined so that the remote user and the local user can be seen in the same scene (as in FIG. 3). This composite result can be transmitted to a local stereoscopic display system. A second computer can act as the network server, which can perform network encoding/decoding tasks as well as depth map generation, for example.

Figure 7:
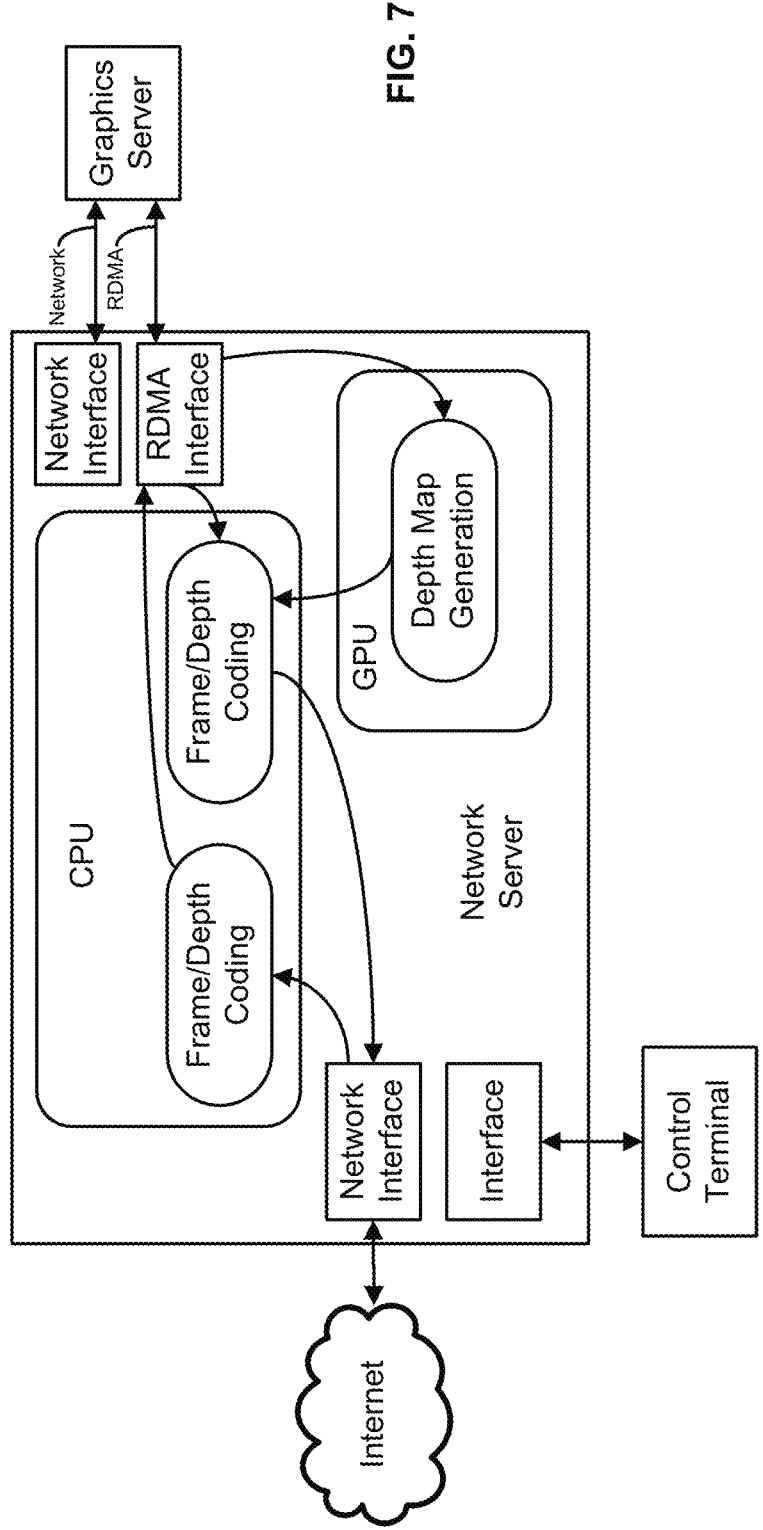
FIG. 7 illustrates exemplary processes performed within a network server.

FIG. 7 illustrates exemplary processes that can be performed with the network server. Local images gathered from the graphics server via the RDMA connection can be analyzed and mapped with depth information, encoded for efficient network transmission, and sent to an external network connection to be received by a corresponding network server at the remote site. Simultaneously, encoded images and depth maps can be received from the remote site, decoded, and provided to the local graphics server via the RDMA connection.

The system can be user-controlled by a control terminal connected to the network server; the user can then access and control the graphics server via the dedicated network connection to the network server.

Parameters of virtual interactive presence can be configured depending on the system used. Configurable parameters include, but are not limited to, size of virtual elements, presence of virtual elements (opaque, translucent, etc.), time of virtual presence (time can be configured to be delayed, slowed, increased, etc.), superimposition of elements such that any combination of virtual and real can be superimposed and/or 'fitted' over one another, and the like.

Figure 8:
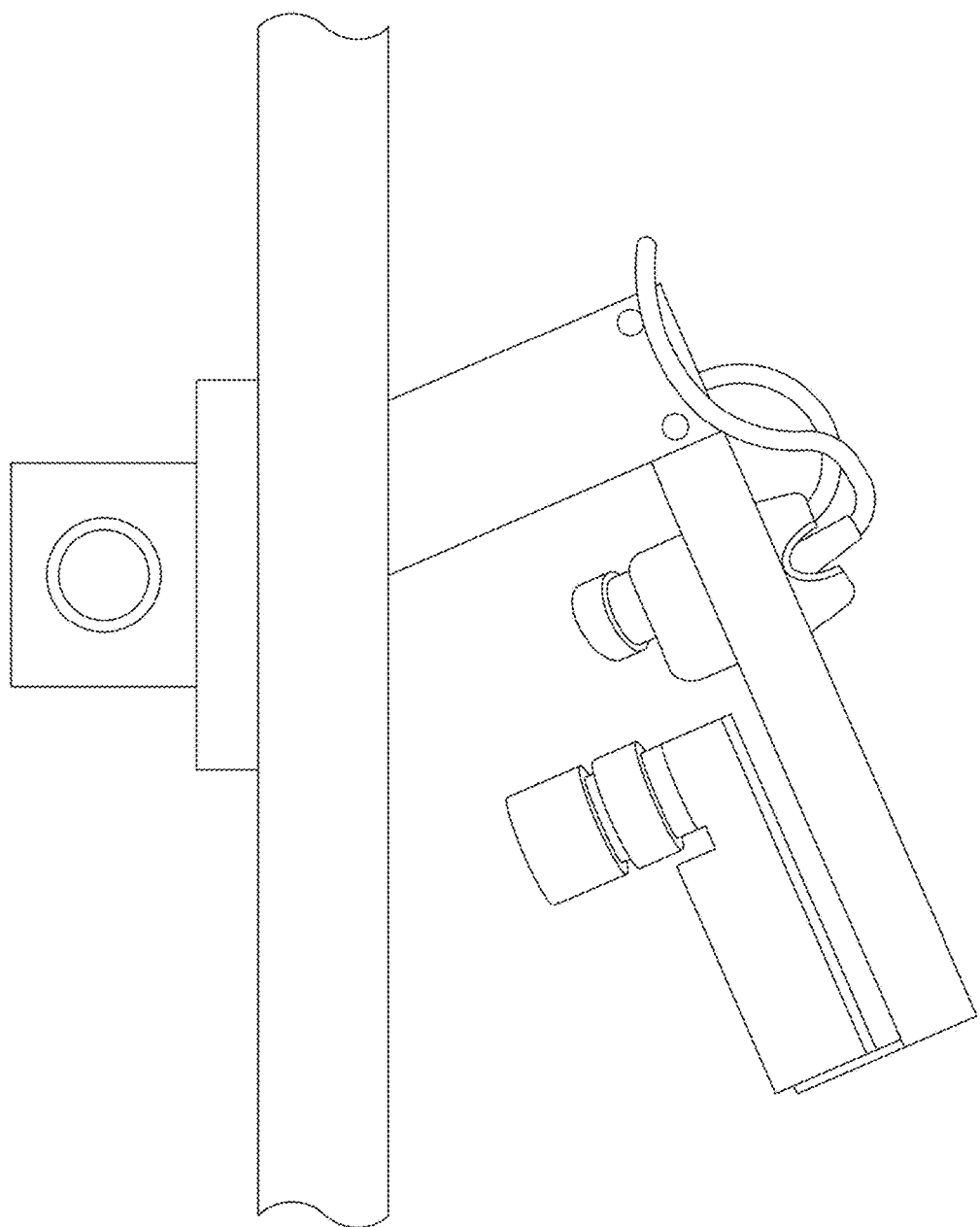
FIG. 8 illustrates a side view of an exemplary VIP display.
Figure 9:
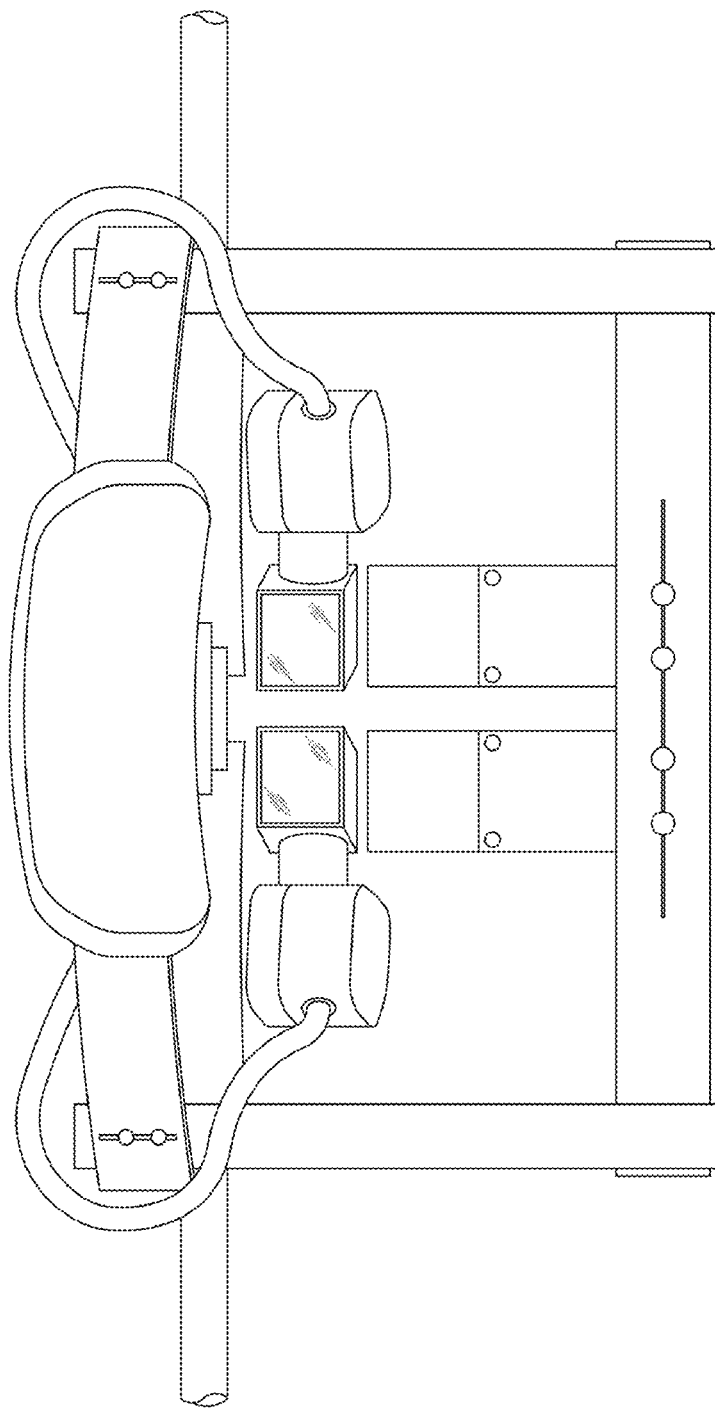
FIG. 9 illustrates a user's view of an exemplary VIP display.
Figure 10:
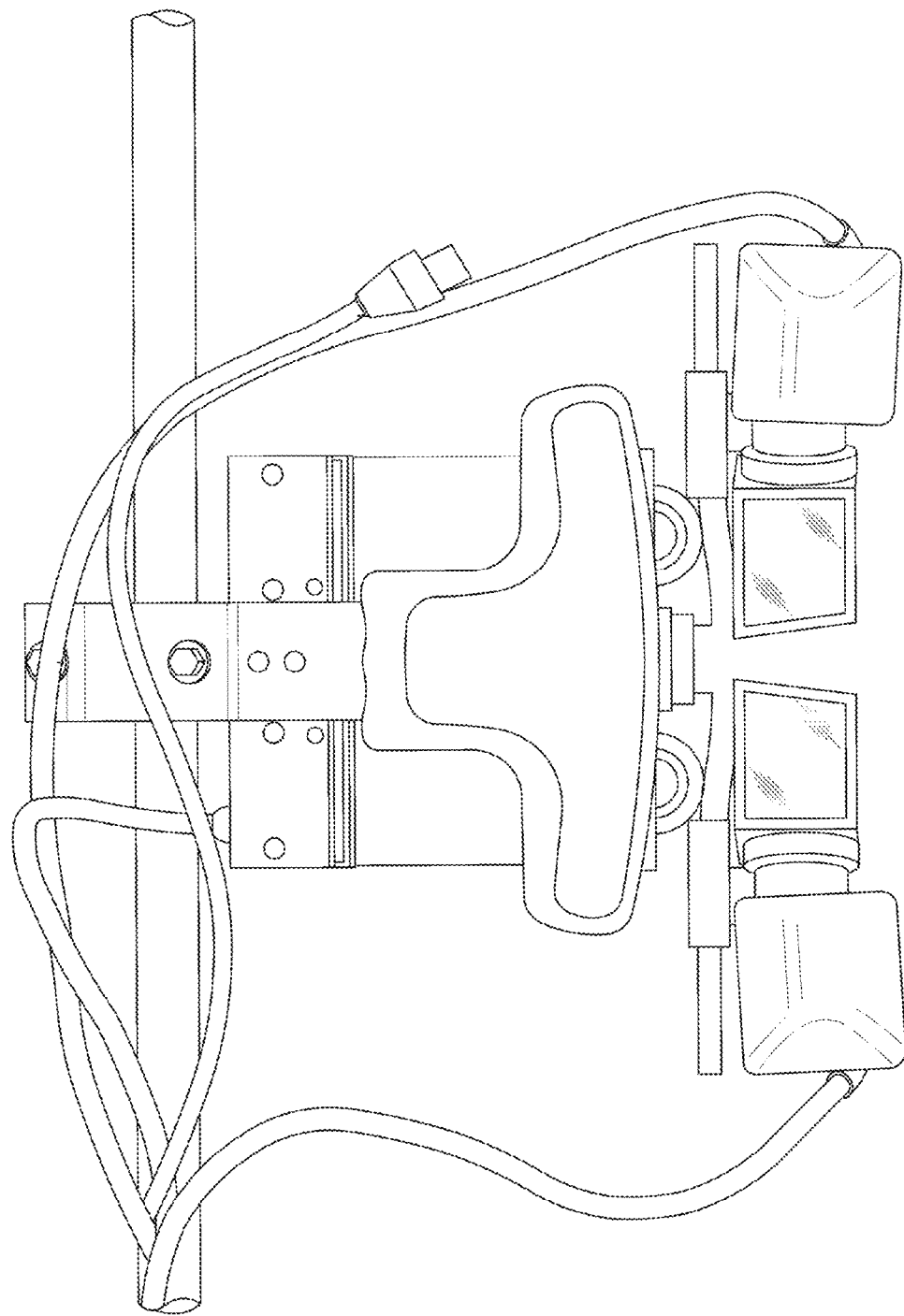
FIG. 10 illustrates a user's view of an exemplary VIP display.

FIG. 8 illustrates a side view of an exemplary VIP display. FIG. 9 illustrates a user's view of an exemplary VIP display. FIG. 10 illustrates a user's view of an exemplary VIP display.

As used herein, a "local" field of interest can refer to a local physical field and local user, thus making every other field remote. Each field can be local to its local physical user, but remote to other users. The composite of the fields can be a common field of interest. This is distinct from common "virtual worlds" in that there can be components of "real" within the local rendering of the common field of interest and interactions can be between actual video (and other) renderings of physical objects and not just graphic avatars representing users and objects. The methods and systems provided allow for virtual interactive presence to modify/optimize a physical domain by the interplay of real and virtual.

Figure 11:
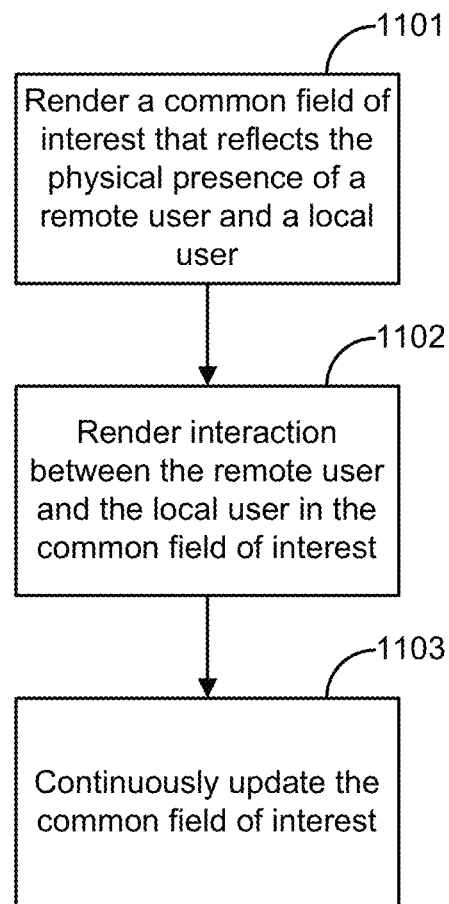
FIG. 11 illustrates an exemplary method.

In an aspect, illustrated in FIG. 11, provided are methods for virtual interactive presence comprising rendering a common field of interest that reflects the physical presence of a remote user and a local user at 1101, rendering interaction between the remote user and the local user in the common field of interest at 1102, and continuously updating the common field of interest such that the presence of the remote user is rendered in real time to the local user and the presence of the local user is rendered in real time to the remote user at 1103.

The common field of interest can be rendered such that the remote user experiences the common field of interest similarly to the local user. The local user can experience the remote user's physical presence in a manner that enables continuous interaction in the common field of interest with the remote user. The methods can further comprise rendering the physical presence of a local object in the common field and rendering interaction between the local user and the local object in the common field. The methods can further comprise rendering the physical presence of a local object in the common field of interest and rendering interaction between the remote user and the local object in the common field of interest.

Figure 12:
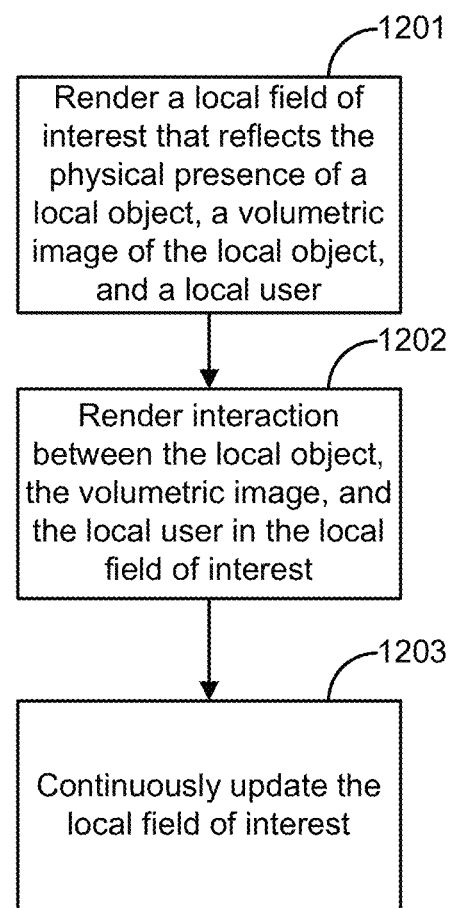
FIG. 12 illustrates another exemplary method.

In another aspect, illustrated in FIG. 12, provided are methods for virtual interactive presence comprising rendering a local field of interest that reflects the physical presence of a local object, a volumetric image of the local object, and a local user at 1201, rendering interaction between the local object, the volumetric image, and the local user in the local field of interest at 1202, and continuously updating the local field of interest such that the presence of the local object and the volumetric image of the local object is rendered in real time to the local user at 1203.

The local object can be, for example, a patient and the volumetric image of the local object can be, for example, a medical image of a part of the patient. However, the local object can be any object of interest and the image of the local object can be any accurate rendering of that object. For example, could be an automobile engine and a 3D graphic of the engine, etc.

The medical image can be, for example, one of, an x-ray image, an MRI image, or a CT image. The methods can further comprise superimposing, by the local user, the volumetric image onto the local object. The superimposition can be performed automatically by a computer.

The methods can further comprise adjusting, by the local user, a property of the volumetric image. The property can be one or more of transparency, spatial location, and scale.

The methods can further comprise rendering a local tool in the local field of interest. The methods can further comprise rendering the local tool in accurate spatial relation to the rendering of the local object. The tool can be any type of tool, for example, a surgical tool.

In another aspect, provided are systems for virtual presence, comprising a virtual presence display, configured for displaying a common field of interest, a local sensor, configured for obtaining local virtual presence data, a network interface, configured for transmitting local virtual presence data and receiving remote virtual presence data, and a processor, coupled to the virtual presence display, the local sensor, and the network interface, wherein the processor is configured to perform steps comprising, rendering a common field of interest that reflects the physical presence of a remote user and a local user based on the local virtual presence data and the remote virtual presence data, rendering interaction between the remote user and the local user in the common field of interest, continuously updating the common field of interest such that the presence of the remote user is rendered in real time to the local user and the presence of the local user is rendered in real time to the remote user, and outputting the common field of interest to the virtual presence display.

The virtual presence display can be one or more of a stereoscopic display, a monoscopic display (such as a CRT, LCD, etc.), and the like. The sensor can be one or more of a camera, an infrared sensor, a depth scan sensor, and the like. The common field of interest can be rendered such that the remote user experiences the common field of interest similarly to the local user. The local user can experience the remote user's physical presence in a manner that enables continuous interaction in the common field of interest with the remote user.

The processor can be further configured to perform steps comprising rendering the physical presence of a local object in the common field of interest and rendering interaction between the local user and the local object in the common field of interest.

The processor can be further configured to perform steps comprising rendering the physical presence of a local object in the common field of interest and rendering interaction between the remote user and the local object in the common field of interest.

Further provided are systems for virtual presence, comprising a virtual presence display, configured for displaying a local field of interest, a local sensor, configured for obtaining local virtual presence data, a processor, coupled to the virtual presence display and the local sensor, wherein the processor is configured to perform steps comprising, rendering a local field of interest that reflects the physical presence of a local object and a local user based on the local virtual presence data and a volumetric image of the local object, rendering interaction between the local object, the volumetric image, and the local user in the local field of interest, continuously updating the local field of interest such that the presence of the local object and the volumetric image of the local object is rendered in real time to the local user, and outputting the local field of interest to the virtual presence display.

The virtual presence display can be one or more of a stereoscopic display, a monoscopic display (such as a CRT, LCD, etc.), and the like. The sensor can be one or more of a camera, an infrared sensor, a depth scan sensor, and the like.

The local object can be, for example, a patient and the volumetric image of the local object can be, for example, a medical image of a part of the patient. The medical image can be, for example, one of, an x-ray image, an MRI image, or a CT image. However, the local object can be any object of interest and the image of the local object can be any accurate rendering of that object. For example, could be an automobile engine and a 3D graphic of the engine, etc.

The processor can be further configured to perform steps comprising superimposing, by the local user, the volumetric image onto the local object. The processor can be further configured to perform steps comprising adjusting, by the local user, a property of the volumetric image. The property can be one or more of transparency, spatial location, and scale.

The processor can be further configured to perform steps comprising rendering a local tool in the local field of interest. The processor can be further configured to perform steps comprising rendering the local tool in accurate spatial relation to the rendered local object.

The disclosed methods and systems can have broad applications. For example, surgery, gaming, mechanics, munitions, battle field presence, instructional efforts (training) and/or any other situation where interaction is part of the scenario.

Also disclosed are methods and systems that enable a remote expert to be virtually present within a local surgical field. Virtual interactive presence can be used to enable two surgeons remote from each other to interactively perform a surgical procedure. The methods and system enable two or more operators to be virtually present, and interactive, within the same real operative field, thus supporting remote assistance and exporting surgical expertise.

The methods and systems can also be used to superimpose imaging data of the operative anatomy onto the anatomy itself for guidance and orientation (augmented reality). The methods and systems can be used for training of students. The methods and systems augment and enhance the field of robotics by virtually bringing an expert into the robotic field to guide the robot operator. The methods and systems are applicable to endoscopic procedures by inserting the expert's hands directly into the endoscopic field for guidance. The methods and systems expand remote surgery by providing the assistance of a remote expert to an actual local surgeon, whose basic skills can handle emergencies, and who will learn from the virtual interaction. The methods and systems can be used at trauma sites and other medical environments. The methods and systems can be used to provide remote assistance in other areas such as engineering, construction, architecture, and the like. The methods and systems disclosed can be used to transmit expertise to a remote 'site of need', merge contemporary imaging directly into the surgical field, and train surgical students An exemplary remote surgical assistance system for transmitting surgical maneuvers of a local expert to a remote surgeon for the purpose of guiding/assisting the remote surgeon is illustrated in FIG. 13. The remote surgical field can be viewed by the remote surgeon with a binocular video system. The video system can show the field with his hands and instruments performing the procedure. The viewing system can be referred to as a surgical videoscope.

The binocular video rendering of the remote field can be transmitted to the local expert), who can view the (now virtual) stereoscopic rendering of the procedure through a second surgical videoscope system. The local expert can insert his hands into the virtual field, thus seeing his real hands within the virtual field.

The video image of the local expert's hands can be transmitted back to the remote surgeon's surgical videoscope system superimposed into the real field. The remote surgeon can then see the expert's virtual hands within his surgical field in a spatially/anatomically relevant context. With this system, the local expert can use his hands to show the remote surgeon how to perform the case.

Exemplary elements of the system can comprise a remote station where the remote surgeon can perform the operative procedure, a remote surgical videoscope system comprised of, for example, a fixed stereoscopic videoscope that may resemble a mounted microscope. This apparatus can be used by the remote surgeon to view the operative field. Any other type of suitable VIP display can be used. The system can project the binocular video image to a similar local surgical videoscope at a local station. The local surgical videoscope can receive the binocular video image of the remote procedure and allow the local expert to view it. The local videoscope can view the local surgeons hands as they move within the virtual remote field as viewed through the local videoscope. The local videoscope can then transmit the local expert's hands back to the remote videoscope so that the remote surgeon can see the expert's virtual hands within the real field.

With this system, the local expert can show the remote surgeon the appropriate maneuvers that result in successful completion of the case. The remote surgeon can have a basic skill set to carry out the new procedure. Therefore, the local expert can simply demonstrates to the remote surgeon new ways to apply the skill set. This system does not have to supplant the remote surgeon, but can be used to enhance his/her capability. The remote surgeon can be on hand to rapidly deal with any emergencies. Time delay is minimized because the remote surgeon can use his/her own hands to perform the task, eliminating the need for the local expert to manipulate remote robotic apparatuses.

Also disclosed are methods and systems for merging contemporary medical imaging onto an operative field. A volume image can be obtained of the operative field. For example, a volume MRI of the head, prior to the surgical procedure. The image data can be reconstructed into a three dimensional rendering of the anatomy. This rendering can be transmitted to the surgical videoscope that will be used to view the operative field. Through the videoscope, the surgeon can view this 3D rendering in a translucent manner superimposed onto the surgical field. In this case, the surgeon would see a rendered head superimposed on the real head. Using software tools in the surgical videoscope interface, the surgeon can rotate and scale the rendered image until it "fits" the real head. The videoscope system can allow the surgeon to differentially fade the rendered head and real head so that the surgeon can "look into" the real head and plan the surgery.

Exemplary elements of the system can comprise a surgical videoscope viewing system through which the surgeon views the surgical field. A computer for reconstruction of a volume-acquired MRI/CT (or other) image with sufficient resolution to enable matching it to the real surgical anatomy. The volume rendered image can be displayed through the videoscope system so that the surgeon can see it stereoscopically. A software interface can enable the surgeon to vary the translucency of the rendered and real anatomy so that the rendered anatomy can be superimposed onto the real anatomy. The surgeon can "open up" the rendered anatomy to view any/all internal details of the image as they relate to the real anatomy. Surgical tools can be spatially registered to the rendered anatomy so that behavior can be tracked and applied to the image.

As shown in FIG. 14, an example of such a task is placing small objects inside a jar of dark gelatin so that they are not visible to the surgeon. The task is for the surgeon to use a long forceps to reach into the gelatin and touch or grasp the objects. The Surgical Videoscope system can obtain a volume scan of the gelatin jar and render the jar in three dimensions and display a binocular rendering through the videoscope. The surgeon can view the rendering and the real jar through the scope system and fit the rendered jar onto the real jar. By differentially adjusting translucency, the surgeon can reach into the real jar with a forceps and grasp a selected object, while avoiding other designated objects.

The grasping instrument can be spatially registered onto the volumetric rendering of the surgical field, thereby allowing a graphic of the tool to be displayed on the rendering of the surgical field in appropriate anatomic orientation. This can provide enhanced guidance. This can be implemented by touching designated landmarks on the real object (jar) with a digitizer that communicates with the image rendering system, thus defining the object/probe relationship. Because the object (jar) is registered to the image of the jar by superimposition, a graphic of the probe can be displayed in relation to the image of the jar enabling virtual surgery.

There are many situations in which the present system can be used. For example, remote surgery, medical training, and tele-medicine, which can be used for third world countries or in a military situation. Surgeons remotely located from patients can assist other surgeons near the patient, can assist medics near the patient, and can perform surgical operations when coupled to a robotic surgery system. Other examples include, augmented or enhanced surgery—normal surgery using virtual environments, an example of which is endoscopic surgery. Surgical procedures can also be simulated. Surgeons located remote from each other may plan and practice a procedure before carrying out the operation on a real patient.

Other applications include the preparation of patient before surgery, medical therapy, preventative medicine, exposure therapy, reducing phobias, training people with disabilities and skill enhancement, and the like.

The viewer then views the projection through passive stereoscopic polarized glasses (similar to sunglasses) that route the left-eye image to the left eye, and the right-eye image to the right eye. This provides an illusion of stereopsis when the correctly-offset images are properly rendered by the software. The system can be replaced by other types of stereoscopic displays with no functional detriment to the system. The stereoscopic display can comprise at least two display projectors fitted with polarizing lenses, a back-projection screen material that maintains light polarization upon diffusion, special glasses that restrict each eye to see only light of a particular polarization, and the viewer. The image to be viewed can be rendered with two slightly different view transformations, reflecting the different locations of the ideal viewer's two eyes. One projector displays the image rendered for the left eye's position, and the other projector displays the image rendered for the right eye's position. The glasses restrict the light so that the left eye sees only the image rendered for it, and the right eye sees only the image rendered for it. The viewer, presented with a reasonable stereoscopic image, will perceive depth.

Figure 15:
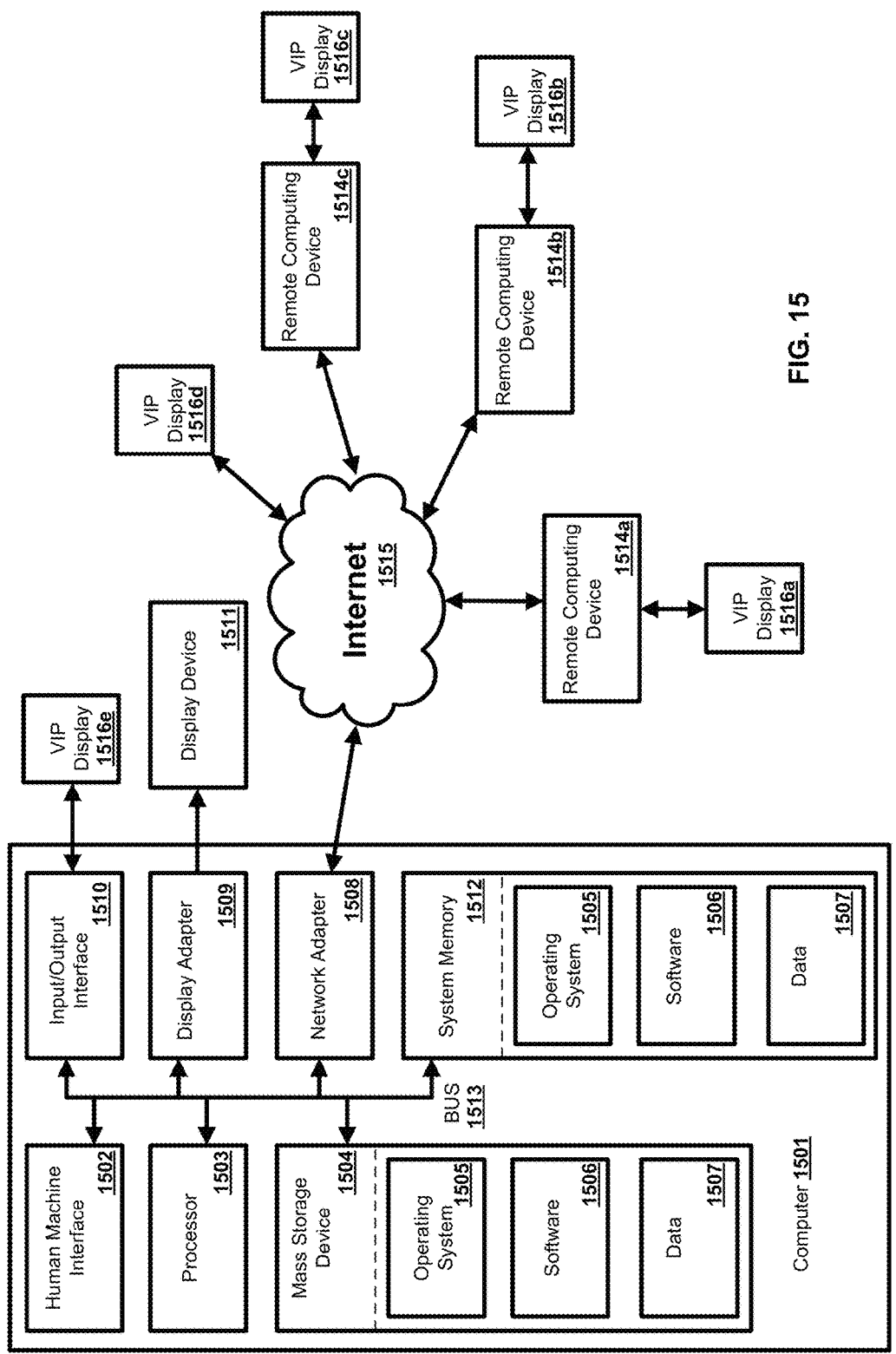
FIG. 15 illustrates an exemplary operational environment.

FIG. 15 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The methods can be operational with numerous other general purpose or special purpose computing system environments or configurations. Examples of well known computing systems, environments, and/or configurations that may be suitable for use with the system and method include, but are not limited to, personal computers, server computers, laptop devices, and multiprocessor systems. Additional examples include set top boxes, programmable consumer electronics, network PCs, minicomputers, mainframe computers, distributed computing environments that include any of the above systems or devices, and the like.

The methods may be described in the general context of computer instructions, such as program modules, being executed by a computer. Generally, program modules include routines, programs, objects, components, data structures, etc. that perform particular tasks or implement particular abstract data types. The system and method may also be practiced in distributed computing environments where tasks are performed by remote processing devices that are linked through a communications network. In a distributed computing environment, program modules may be located in both local and remote computer storage media including memory storage devices.

The methods disclosed herein can be implemented via one or more general-purpose computing devices in the form of a computer 1501. The components of the computer 1501 can include, but are not limited to, one or more processors or processing units 1503, a system memory 1512, and a system bus 1513 that couples various system components including the processor 1503 to the system memory 1512.

The system bus 1513 represents one or more of several possible types of bus structures, including a memory bus or memory controller, a peripheral bus, an accelerated graphics port, and a processor or local bus using any of a variety of bus architectures. By way of example, such architectures can include an Industry Standard Architecture (ISA) bus, a Micro Channel Architecture (MCA) bus, an Enhanced ISA (EISA) bus, a Video Electronics Standards Association (VESA) local bus, and a Peripheral Component Interconnects (PCI) bus also known as a Mezzanine bus. This bus, and all buses specified in this description can also be implemented over a wired or wireless network connection. The bus 1513, and all buses specified in this description can also be implemented over a wired or wireless network connection and each of the subsystems, including the processor 1503, a mass storage device 1504, an operating system 1505, application software 1506, data 1507, a network adapter 1508, system memory 1512, an Input/Output Interface 1510, a display adapter 1509, a display device 1511, and a human machine interface 1502, can be contained within one or more remote computing devices 1514a,b,c at physically separate locations, connected through buses of this form, in effect implementing a fully distributed system.

The computer 1501 typically includes a variety of computer readable media. Such media can be any available media that is accessible by the computer 1501 and includes both volatile and non-volatile media, removable and non-removable media. The system memory 1512 includes computer readable media in the form of volatile memory, such as random access memory (RAM), and/or non-volatile memory, such as read only memory (ROM). The system memory 1512 typically contains data such as data 1507 and/or program modules such as operating system 1505 and application software 1506 that are immediately accessible to and/or are presently operated on by the processing unit 1503.

The computer 1501 may also include other removable/non-removable, volatile/non-volatile computer storage media. By way of example, FIG. 15 illustrates a mass storage device 1504 which can provide non-volatile storage of computer code, computer readable instructions, data structures, program modules, and other data for the computer 1501. For example, a mass storage device 1504 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules can be stored on the mass storage device 1504, including by way of example, an operating system 1505 and application software 1506. Each of the operating system 1505 and application software 1506 (or some combination thereof) may include elements of the programming and the application software 1506. Data 1507 can also be stored on the mass storage device 1504. Data 1507 can be stored in any of one or more databases known in the art. Examples of such databases include, DB2®, Microsoft® Access, Microsoft® SQL Server, Oracle®, mySQL, PostgreSQL, and the like. The databases can be centralized or distributed across multiple systems.

A user can enter commands and information into the computer 1501 via an input device (not shown). Examples of such input devices include, but are not limited to, a keyboard, pointing device (e.g., a "mouse"), a microphone, a joystick, a serial port, a scanner, tactile input devices such as gloves, and other body coverings, and the like. These and other input devices can be connected to the processing unit 1503 via a human machine interface 1502 that is coupled to the system bus 1513, but may be connected by other interface and bus structures, such as a parallel port, game port, or a universal serial bus (USB).

A display device 1511 can also be connected to the system bus 1513 via an interface, such as a display adapter 1509. A computer 1501 can have more than one display adapter 1509 and a computer 1501 can have more than one display device 1511. For example, a display device can be a monitor, an LCD (Liquid Crystal Display), or a projector. In addition to the display device 1511, other output peripheral devices can include components such as speakers (not shown) and a printer (not shown) which can be connected to the computer 1501 via Input/Output Interface 1510.

The computer 1501 can operate in a networked environment using logical connections to one or more remote computing devices 1514a,b,c. By way of example, a remote computing device can be a personal computer, portable computer, a server, a router, a network computer, a peer device or other common network node, and so on. Logical connections between the computer 1501 and a remote computing device 1514a,b,c can be made via a local area network (LAN) and a general wide area network (WAN). Such network connections can be through a network adapter 1508. A network adapter 1508 can be implemented in both wired and wireless environments. Such networking environments are commonplace in offices, enterprise-wide computer networks, intranets, and the Internet 1515.

One or more VIP displays 1516a,b,c,d,e can communicate with the computer 1501. In one aspect, VIP display 1516e can communicate with computer 1501 through the input/output interface 1510. This communication can be wired or wireless. Remote VIP displays 1516a,b,c can communicate with computer 1501 by communicating first with a respective remote computing device 1514a,b,c which then communicates with computer 1501 through the network adapter 1508 via a network such as the Internet 1515. Remote VIP display 1516d can communicate with computer 1501 without the need for a remote computing device. Remote VIP display 1516d can communicate via a network, such as the Internet 1515. The VIP displays 1516a,b,c,d,e can communicate wireless or through a wired connection. The VIP displays 1516a,b,c,d,e can communicate individual or collectively as part of a VIP display network.

For purposes of illustration, application programs and other executable program components such as the operating system 1505 are illustrated herein as discrete blocks, although it is recognized that such programs and components reside at various times in different storage components of the computing device 1501, and are executed by the data processor(s) of the computer. An implementation of application software 1506 may be stored on or transmitted across some form of computer readable media. Computer readable media can be any available media that can be accessed by a computer. By way of example, and not limitation, computer readable media may comprise "computer storage media" and "communications media." "Computer storage media" include volatile and non-volatile, removable and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the inventive concepts or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made in the present methods and systems without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method for image registration comprising:
    receiving a first image from a local device, the first image comprising a representation of a first element, wherein the first image has a first alignment and orientation when viewed relative to a coordinate system;
    receiving a second image from a remote device, the second image comprising a representation of a second element physically disposed remotely from the first element, wherein, prior to transmission, the second image had a second alignment and orientation when viewed relative to the coordinate system, and wherein the second image is received in a transformed state resulting, at least in part, from a skew, shift, crop, translation, or combination thereof of the second image during transmission such that display of the second image in the transformed state results in a transformed alignment and orientation different from the second alignment and orientation;
    generating a common field of interest based on the first image and the second image such that the presence of at least one of the first element and the second element is spatially registered relative to the other of the first element and the second element, wherein generating the common field of interest comprises a de-transformation of at least the second image and wherein the de-transformation comprises applying one or more image transforms to one or more of the first image and the second image, and wherein the one or more image transforms are based on a first transformation characteristic of one or more of the local device and the remote device and a second transformation characteristic resulting from transmission of one or more of the first image and the second image, wherein the de-transformation of at least the second image facilitates display of the second image having the second alignment and orientation when viewed relative to the coordinate system; and
    rendering the common field of interest, wherein the first element and the second element in the common field of interest are rendered to a remote viewer and a local viewer with a substantially similar alignment and orientation.

2. The method of claim 1, further comprising rendering the presence of each of the first element and the second element in real time, wherein each of the first element and the second element is registered relative to another of the elements.

3. The method of claim 1, further comprising the step of rendering interaction between the first element and the second element in the common field of interest.

4. The method of claim 1, further comprising the step of continuously updating the common field of interest such that the presence of the first element and the second element is rendered in real time to a local viewer.

5. The method of claim 1, further comprising the step of continuously updating the common field of interest such that the presence of the first element and the second element is rendered in real time to a remote viewer.

6. The method of claim 1, further comprising the step of calibrating the common field of interest by aligning a calibration feature of a remote field and a calibration feature of a local field, wherein the calibration feature is transmitted from the remote device to the local device and is transformed during transmission, and wherein a de-transformation of the calibration feature facilitates determination of the one or more image transforms applied to one or more of the first image and the second image.

7. The method of claim 6, wherein the calibration features of the remote field and the local field are aligned relative to the coordinate system.

8. The method of claim 6, wherein the calibration features of the remote field and the local field are aligned relative to a pre-defined virtual fiducial.

9. The method of claim 1, wherein the second image comprises a registration mechanism and wherein the registration mechanism is received in a transformed state resulting, at least in part, from a skew, shift, crop, translation, or combination thereof of the registration mechanism during transmission.

10. A method for image registration comprising:
generating, using a local device, a first image representing a first element having a first alignment and orientation when viewed relative to a coordinate system;
generating, using a remote device, a second image representing a second element having a second alignment and orientation when viewed relative to the coordinate system, wherein the second element is physically disposed remotely from the first element, and wherein at least one of the first image and the second image is part of a live video stream;
determining an image transform based on a transformed state of one or more of the first image and the second image, the transformed state altering one or more of the first orientation and alignment and the second orientation and alignment, wherein the transformed state of the one or more of the first image and the second image is based, at least in part, on a skew, shift, crop, translation, or combination thereof of the one or more of the first image and the second image caused by transmission of the one or more of the first image and the second image due at least in part to compression or decompression, or both of the one or more of the first image and the second image, and wherein the transformed state is based on a transformation characteristic of each of the local device and the remote device; and
rendering a composite image including the first image and the second image, wherein at least one of the first image and the second image is spatially registered relative to the other of the first image and the second image based upon a registration feature inserted onto at least one of the first image and the second image, wherein the first image and the second image in the composite image are rendered to a remote viewer and a local viewer with a substantially similar alignment and orientation, wherein rendering the composite image comprises a de-transformation of one or more of the first image and the second image, wherein the de-transformation comprises applying the image transform to one or more of the first image and the second image, and wherein the de-transformation facilitates display of the first image having the first orientation and alignment and the second image having the second orientation and alignment.

11. The method according to claim 10, wherein the registration feature is a third image inserted onto at least one of the first image and the second image.

12. The method of claim 10, wherein the registration feature is a virtual image rendered in the common field of interest.

13. The method of claim 10, wherein at least one of the first image and the second image is part of a video stream.

14. The method of claim 10, further comprising the step of continuously updating the composite image to render the composite image in real time to at least one of a local viewer and a remote viewer.

15. A system for image registration comprising:
a display configured for displaying a common field of interest;
a sensor configured for obtaining image data;
a processor in signal communication with the display and the sensor,
wherein the processor is configured to perform steps comprising,
generating, based at least on the image data, a first image representing a first element having a first alignment and orientation when viewed relative to a coordinate system;
receiving a second image representing a second element having a second alignment and orientation when viewed relative to the coordinate system, wherein the second element is physically disposed remotely from the first element, and wherein at least one of the first image and the second image is part of a live video stream;
determining an image transform based on a transformed state of one or more of the first image and the second image, the transformed state altering one or more of the first orientation and alignment and the second orientation and alignment, wherein the transformed state of the one or more of the first image and the second image is based, at least in part, on a skew, shift, crop, translation, or combination thereof of the one or more of the first image and the second image caused by transmission of the one or more of the first image and the second image due at least in part to compression or decompression, or both of the one or more of the first image and the second image, and wherein the transformed state is based on a transformation characteristic of each of the local device and the remote device; and
rendering a composite image including the first image and the second image, wherein at least one of the first image and the second image is spatially registered relative to the other of the first image and the second image based upon a registration feature inserted onto at least one of the first image and the second image, wherein the first image and the second image in the composite image are rendered to a remote viewer and a local viewer with a substantially similar alignment and orientation, wherein rendering the composite image comprises a de-transformation of one or more of the first image and the second image, and wherein the de-transformation facilitates display of the first image having the first orientation and alignment and the second image having the second orientation and alignment.

16. The system of claim 15, wherein the sensor is at least one of a camera, an infrared sensor, a light sensor, a RADAR device, a SONAR device, and a depth scan sensor.

17. The system of claim 15, wherein the processor is configured to perform the step of continuously updating the common field of interest such that the presence of the remote element is rendered in real time to a local viewer.

18. The system of claim 15, wherein the processor is configured to perform the step of continuously updating the common field of interest such that the presence of a local one of the elements is rendered in real time to a remote viewer.

* * * * *